(12) United States Patent
Mauldin, Jr. et al.

(10) Patent No.: US 10,368,834 B2
(45) Date of Patent: Aug. 6, 2019

(54) BONE SURFACE IMAGE RECONSTRUCTION USING ULTRASOUND

(75) Inventors: F. William Mauldin, Jr., Charlottesville, VA (US); John A. Hossack, Charlottesville, VA (US); Kevin Owen, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/113,672

(22) PCT Filed: Apr. 25, 2012

(86) PCT No.: PCT/US2012/034945
§ 371 (c)(1),
(2), (4) Date: Nov. 1, 2013

(87) PCT Pub. No.: WO2012/148985
PCT Pub. Date: Nov. 1, 2012

(65) Prior Publication Data
US 2014/0046186 A1  Feb. 13, 2014

Related U.S. Application Data

(60) Provisional application No. 61/479,072, filed on Apr. 26, 2011, provisional application No. 61/547,175, (Continued)

(51) Int. Cl.
*A61B 8/08* (2006.01)
*A61B 8/00* (2006.01)
(Continued)

(52) U.S. Cl.
CPC .......... *A61B 8/0875* (2013.01); *A61B 8/4254* (2013.01); *A61B 8/4455* (2013.01);
(Continued)

(58) Field of Classification Search
CPC ... A61B 8/0841; A61B 8/0875; A61B 8/4254; A61B 2017/3413; A61B 34/20;
(Continued)

(56) References Cited

U.S. PATENT DOCUMENTS 4,363,326 A  12/1982  Kopel
5,259,386 A  11/1993  Sharkawy
(Continued)

FOREIGN PATENT DOCUMENTS

CN  102008318 A  4/2011
EP  0891743 A1  1/1999
(Continued)

OTHER PUBLICATIONS

Chen, Ultrasound Guided Spine Needle Insertion, Medical Imaging 2010: Visualization, Image-Guided Procedures, and Modeling, Proc. of SPIE vol. 7625, 762538.*
(Continued)

*Primary Examiner* — Bo Joseph Peng
(74) *Attorney, Agent, or Firm* — Schwegman Lundberg & Woessner, P.A.

(57) ABSTRACT

An ultrasonic transducer element can configured to generate ultrasonic energy directed into tissue of a subject and configured to receive a portion of the ultrasonic energy reflected by a target located within the tissue. The ultrasonic transducer can include a surface configured to provide or receive the ultrasonic energy, the surface including an area of greater than or equal to about $4\lambda^2$, or the ultrasonic transducer element can be included in an array having a spacing between at least two adjacent ultrasound elements of less than or equal to about $\frac{1}{2}\lambda$, and the array comprising an aperture that is at least approximately symmetrical in two axes. A three-dimensional representation of one or more of
(Continued)

a location, shape, or orientation of at least a portion of the target can be presented via the display.

27 Claims, 23 Drawing Sheets

Related U.S. Application Data filed on Oct. 14, 2011, provisional application No. 61/569,685, filed on Dec. 12, 2011, provisional application No. 61/597,317, filed on Feb. 10, 2012.

(51) Int. Cl.
| | | |
|---|---|---|
| *G01S 7/52* | (2006.01) | |
| *G01S 15/60* | (2006.01) | |
| *G01S 15/89* | (2006.01) | |
| *A61B 34/20* | (2016.01) | |
| *A61B 17/34* | (2006.01) | |
| *A61B 90/00* | (2016.01) | |

(52) U.S. Cl.
CPC .......... *A61B 8/4466* (2013.01); *A61B 8/4483* (2013.01); *A61B 34/20* (2016.02); *G01S 7/5208* (2013.01); *G01S 7/52073* (2013.01); *G01S 15/60* (2013.01); *G01S 15/8915* (2013.01); *A61B 8/0841* (2013.01); *A61B 8/4245* (2013.01); *A61B 8/4433* (2013.01); *A61B 8/466* (2013.01); *A61B 8/483* (2013.01); *A61B 2017/3413* (2013.01); *A61B 2034/2048* (2016.02); *A61B 2034/2051* (2016.02); *A61B 2034/2055* (2016.02); *A61B 2090/378* (2016.02); *A61B 2090/3937* (2016.02); *G01S 15/899* (2013.01)

(58) Field of Classification Search
CPC ... A61B 8/4483; A61B 8/4466; A61B 8/4455; A61B 2090/3937; A61B 2090/378; A61B 2034/2051; A61B 2034/2055; A61B 2034/2048; A61B 8/4245; A61B 8/483; A61B 8/466; A61B 8/4433; G01S 15/8915; G01S 7/52073; G01S 15/60; G01S 7/5208; G01S 15/899
See application file for complete search history.

(56) References Cited

U.S. PATENT DOCUMENTS

| | | | |
|---|---|---|---|
| 5,546,949 A | 8/1996 | Frazin et al. | |
| 5,623,931 A | 4/1997 | Wung et al. | |
| 5,655,535 A | 8/1997 | Friemel et al. | |
| 5,685,308 A * | 11/1997 | Wright ................ | G01S 7/52023 600/443 |
| 5,722,412 A | 3/1998 | Pflugrath | |
| 5,782,766 A * | 7/1998 | Weng ...................... | A61B 8/463 128/916 |
| 5,806,521 A | 9/1998 | Morimoto et al. | |
| 5,833,627 A | 11/1998 | Shmulewitz et al. | |
| 5,924,992 A | 7/1999 | Park et al. | |
| 5,957,844 A | 9/1999 | Dekel et al. | |
| 6,106,464 A * | 8/2000 | Bass et al. ............ | 600/439 |
| 6,203,498 B1 | 3/2001 | Bunce et al. | |
| 6,296,614 B1 | 10/2001 | Pruter | |
| 6,338,716 B1 | 1/2002 | Hossack et al. | |
| 6,641,537 B2 | 11/2003 | Morris et al. | |
| 6,656,136 B1 * | 12/2003 | Weng ................... | A61B 8/4422 600/407 |
| 6,692,439 B1 | 2/2004 | Walker et al. | |
| 6,733,458 B1 * | 5/2004 | Steins ................... | A61B 8/0833 600/461 |
| 6,964,639 B2 | 11/2005 | Sela et al. | |
| 7,244,234 B2 | 7/2007 | Ridley et al. | |
| 7,402,136 B2 | 7/2008 | Hossack et al. | |
| 7,578,819 B2 | 8/2009 | Bleich et al. | |
| 7,645,238 B2 | 1/2010 | Hirsh | |
| 7,699,776 B2 | 4/2010 | Walker et al. | |
| 7,750,537 B2 | 7/2010 | Hossack et al. | |
| 7,806,823 B2 | 10/2010 | Sakai et al. | |
| 9,579,120 B2 | 2/2017 | Mauldin et al. | |
| 2003/0073895 A1 | 4/2003 | Nields et al. | |
| 2004/0127790 A1 | 7/2004 | Lang et al. | |
| 2004/0158154 A1 | 8/2004 | Hanafy et al. | |
| 2005/0096543 A1 | 5/2005 | Jackson et al. | |
| 2005/0154302 A1 | 7/2005 | Sela et al. | |
| 2005/0154303 A1 * | 7/2005 | Walker ................ | G01S 15/8979 600/443 |
| 2005/0228281 A1 | 10/2005 | Nefos | |
| 2006/0052697 A1 | 3/2006 | Hossack et al. | |
| 2006/0064010 A1 | 3/2006 | Cannon, Jr. et al. | |
| 2006/0100516 A1 | 5/2006 | Hossack et al. | |
| 2006/0206178 A1 | 9/2006 | Kim | |
| 2006/0264745 A1 | 11/2006 | Da Silva | |
| 2007/0016022 A1 | 1/2007 | Blalock et al. | |
| 2007/0016030 A1 | 1/2007 | Stringer | |
| 2007/0016044 A1 | 1/2007 | Blalock et al. | |
| 2007/0034731 A1 | 2/2007 | Falco | |
| 2007/0073155 A1 | 3/2007 | Park et al. | |
| 2007/0156126 A1 | 7/2007 | Flaherty | |
| 2007/0213616 A1 * | 9/2007 | Anderson ................ | A61N 7/02 600/448 |
| 2008/0004481 A1 | 1/2008 | Bax et al. | |
| 2008/0015442 A1 | 1/2008 | Watson et al. | |
| 2008/0091678 A1 | 4/2008 | Walker et al. | |
| 2009/0043205 A1 | 2/2009 | Pelissier et al. | |
| 2009/0142741 A1 | 6/2009 | Ault et al. | |
| 2009/0143674 A1 | 6/2009 | Nields et al. | |
| 2009/0264757 A1 * | 10/2009 | Yang et al. ................ | 600/443 |
| 2009/0279763 A1 | 11/2009 | Langeland et al. | |
| 2009/0299184 A1 | 12/2009 | Walker et al. | |
| 2009/0304246 A1 | 12/2009 | Walker et al. | |
| 2009/0306509 A1 | 12/2009 | Pedersen et al. | |
| 2010/0010348 A1 * | 1/2010 | Halmann ................ | A61B 8/00 600/443 |
| 2010/0016726 A1 * | 1/2010 | Meier ...................... | A61B 8/00 600/459 |
| 2010/0063399 A1 | 3/2010 | Walker et al. | |
| 2010/0142781 A1 | 6/2010 | Walker et al. | |
| 2010/0168578 A1 | 7/2010 | Garson, Jr. | |
| 2010/0249591 A1 | 9/2010 | Heimdal | |
| 2010/0268086 A1 | 10/2010 | Walker et al. | |
| 2010/0298704 A1 | 11/2010 | Pelissier et al. | |
| 2010/0312120 A1 | 12/2010 | Meier | |
| 2011/0166451 A1 | 7/2011 | Blaivas | |
| 2011/0301451 A1 * | 12/2011 | Rohling ................... | A61B 8/00 600/424 |
| 2011/0313288 A1 * | 12/2011 | Chi Sing ............... | A61B 5/0507 600/437 |
| 2012/0157834 A1 | 6/2012 | Lazebnik | |
| 2012/0296213 A1 | 11/2012 | Mauldin, Jr. et al. | |
| 2013/0172743 A1 | 7/2013 | Brewer et al. | |
| 2013/0310688 A1 * | 11/2013 | Rosen ...................... | A61B 8/08 600/437 |
| 2014/0350390 A1 | 11/2014 | Kudavelly et al. | |

FOREIGN PATENT DOCUMENTS

| | | |
|---|---|---|
| EP | 2113192 A1 | 11/2009 |
| GB | 2400176 A | 10/2004 |
| JP | 2010012160 A | 1/2010 |
| JP | 2010527277 A | 8/2010 |
| JP | 2014515685 A | 7/2014 |
| JP | 6381618 B2 | 8/2018 |
| WO | WO-2001001866 A1 | 1/2001 |
| WO | WO-0113796 A1 | 3/2001 |
| WO | WO-03057000 A2 | 7/2003 |
| WO | WO-2003075769 A1 | 9/2003 |
| WO | WO-2004064619 A2 | 8/2004 |
| WO | WO-2004064620 A2 | 8/2004 |
| WO | WO-2004065978 A2 | 8/2004 |

(56) References Cited

FOREIGN PATENT DOCUMENTS

| WO | WO-2005014079 A2 | 2/2005 | | |
|---|---|---|---|---|
| WO | WO-2006042067 A2 | 4/2006 | | |
| WO | WO-2007027511 A2 | 3/2007 | | |
| WO | WO-2007035765 A2 | 3/2007 | | |
| WO | WO-2008144449 A2 | 11/2008 | | |
| WO | WO-2008154632 A2 | 12/2008 | | |
| WO | WO-2009026644 A1 | 3/2009 | | |
| WO | WO-2010021709 A1 | 2/2010 | | |
| WO | WO-2010057315 A1 | 5/2010 | | |
| WO | WO-2010106379 A1 | 9/2010 | | |
| WO | WO-2011094585 A1 | 8/2011 | | |
| WO | WO 2012018851 A1 * | 2/2012 | ........... | A61B 8/0875 |
| WO | WO-2012148985 A1 | 11/2012 | | |
| WO | WO-2012148985 A8 | 11/2012 | | |
| WO | WO-2015025183 A1 | 2/2015 | | |

OTHER PUBLICATIONS

Khallaghi, Registration of a Statistical Shape Model of the Lumbar SPine to 3D Ultrasound Images, Medical Image Computing and Computer-Assisted Intervention—MICCAI 2010, vol. 6362 of the series Lecture Notes in Computer Science pp. 68-75.*
Wachinger, Estimation of acoustic impedance from multiple ultrasound images with application to spatial compounding, Computer Vision and Pattern Recognition Workshops, 2008. CVPRW '08.*
Basarab, Two-dimensional least-squares estimation for motion tracking in ultrasound elastography, Proceedings of the 29th Annual International Conference of the IEEE EMBS Cité Internationale, Lyon, France, Aug. 23-26, 2007.*
Cootes, Active Shape Models—Their Training and Application, Computer Vision and Image Understanding, vol. 61, Issue 1, Jan. 1995, pp. 38-59.*
U.S. Appl. No. 13/574,738, filed Jul. 23, 2012, Ultrasound for Locating Anatomy or Probe Guidance.
"U.S. Appl. No. 13/574,738, Non Final Office Action dated Sep. 25, 2013", 15 pgs.
"U.S. Appl. No. 13/574,738, Preliminary Amendment dated Jul. 23, 2012", 3 pgs.
"International Application Serial No. PCT/US2011/022984, International Preliminary Report on Patentability dated Aug. 9, 2012", 8 pgs.
"International Application Serial No. PCT/US2011/022984, Search Report dated Apr. 7, 2011", 4 pgs.
"International Application Serial No. PCT/US2011/022984, Written Opinion dated Apr. 7, 2011", 11 pgs.
"International Application Serial No. PCT/US2012/034945, International Search Report dated Aug. 7, 2012", 3 pgs.
"International Application Serial No. PCT/US2012/034945, Written Opinion dated Aug. 7, 2012", 7 pgs.
"Selected screen captures obtained Jul. 19, 2012 from Windows Media File (.WMV) titled "Project Lumbar," submitted herewith", (Jul. 19, 2012), 19 pgs.
"SieScape Panoramic Imaging Expanding your field of view in real time", Siemens Medical, (2003), 4 pgs.
"Signostics Brochure", (2010), 4 pgs.
"The Minivisor", [Online]. Retrieved from the Internet: <URL: http://www.ob-ultrasound.net/minivisor.html>, (Accessed Jan. 12, 2011), 2 pgs.
"The Signos, Self Contained Handheld Ultrasound Gains FDA Approval", http://medgadget.com/archives/2009/05/the_signos_self_contained_handheld_ultrasound_gains_fda_approval.html, (May 20, 2009), 5 pgs.
"VMUT—Freehand 3D Ultrasound", Virginia Medical Ultrasound Technology Group, [Online]. Retrieved from the Internet: <URL: http://hobbes.ee.virginia.edu/ultra/ibeam.html>, (Accessed Jan. 19, 2011), 1 pg.
"Windows Media File, "Project Lumbar" submitted herewith in electronic form on compact disc", believed posted on www.youtube.com on Dec. 1, 2009, (Dec. 1, 2009).

Ellis, Michael A, et al., "Super-Resolution Image Reconstruction Using Diffuse Source Models", Ultrasound in Med.& Biol., vol. 36, No. 6, (2010), 967-977.
Fuller, M. I, et al., "Real time imaging with the Sonic Window: A pocket-sized, C-scan, medical ultrasound device", 2009 IEEE International Ultrasonics Symposium (IUS), (2009), 196-199.
Jensen, J Arendt, et al., "Calculation of Pressure Fields from Arbitrarily Shaped, Apodized, and Excited Ultrasound Transducers", IEEE Transactions on Ultrasonics, Ferroelectrics and Frequency Control vol. 39, No. 2, (Mar. 1992), 262-267.
Karaman, Mustafa, et al., "Synthetic Aperture Imaging for Small Scale Systems", IEEE Transactions on Ultrasonics, Ferroelectrics, and Frequency Control vol. 42, No. 3, (May 1995), 429-442.
Klein, Stephen M, et al., "Piezoelectric Vibrating Needle and Catheter for Enhancing Ultrasound-Guided Peripheral Nerve Blocks", Anesthesia & Analgesia, vol. 105 No. 6, (Dec. 2007), 1858-1860.
Murphy, Kevin P, et al., "Loopy Belief Propagation for Approximate Inference: An Empirical Study", UAI'99 Proceedings of the Fifteenth conference on Uncertainty in artificial intelligence, Computer Science Division, University of California Bekeley, (1999), 467-475.
O'Donnell, Matthew, "Coded Excitation System for Improving the Penetration of Real-Time Phased-Array Imaging Systems", IEEE Transactions on Ultrasonics, Ferroelectrics, and Frequency Control vol. 39, No. 3, (May 1992), 341-351.
Parmar, Biren J, et al., "Characterization of controlled bone defects using 2D and 3D ultrasound imaging techniques", Physics in Medicine and Biology, vol. 55, (2010), 4839-4859.
Viola, et al., "Time-Domain Optimized Near-Field Estimator for Ultrasound Imaging : Initial 1-40", IEEE Transactions on Medical Imaging 27(1), (Jan. 2008), 99-110.
Woo, Joseph, "A short History of the development of Ultrasound in Obstetrics and Gynecology", Part 2, [Online]. Retrieved from the Internet: <URL: http://www.ob-ultrasound.net/history2.html>, (Accessed Oct. 29, 2013), 32 pgs.
"Chinese Application Serial No. 201180016949.5, Office Action dated Sep. 18, 2014", w/English Translation, 35 pgs.
"U.S. Appl. No. 13/574,738, Non Final Office Action dated Mar. 3, 2015", 13 pgs.
"U.S. Appl. No. 13/574,738, Response filed Jun. 3, 2015 to Non Final Office Action dated Mar. 3, 2015", 14 pgs.
"U.S. Appl. No. 13/574,738, Advisory Action dated Aug. 7, 2014", 3 pgs.
"U.S. Appl. No. 13/574,738, Examiner Interview Summary dated Aug. 7, 2014", 3 pgs.
"U.S. Appl. No. 13/574,738, Final Office Action dated Mar. 27, 2014", 17 pgs.
"U.S. Appl. No. 13/574,738, Response filed Jul. 23, 2014 to Final Office Action dated Mar. 27, 2014", 16 pgs.
"U.S. Appl. No. 13/574,738, Response filed Sep. 23, 2014 to Advisory Action dated Aug. 7, 2014", 17 pgs.
"U.S. Appl. No. 13/574,738, Response filed Nov. 27, 2013 to Non Final Office Action dated Sep. 25, 2013", 16 pgs.
"Chinese Application Serial No. 201180016949.5, Office Action dated Mar. 25, 2014", w/English Translation, 27 pgs.
"Chinese Application Serial No. 201180016949.5, Response filed Aug. 7, 2014 to Office Action dated Mar. 25, 2014", w/ English Translation of Claims, 19 pgs.
"European Application Serial No. 12777556.7, Office Action dated Dec. 3, 2013", 3 pgs.
"European Application Serial No. 12777556.7, Response filed May 28, 2014 to Office Action dated Dec. 3, 2013", 10 pgs.
"International Application Serial No. PCT/US2012/034945, International Preliminary Report on Patentability dated Nov. 7, 2013", 9 pgs.
"European Application Serial No. 12777556.7, Extended European Search Report dated Aug. 13, 2015", 12 pgs.
"U.S. Appl. No. 13/574,738, Advisory Action dated Feb. 16, 2016", 6 pgs.
"U.S. Appl. No. 13/574,738, Final Office Action dated Oct. 23, 2015", 15 pgs.
"U.S. Appl. No. 13/574,738, Response filed Mar. 16, 2016 to Advisory Action dated Feb. 16, 2016", 14 pgs.

(56) References Cited

OTHER PUBLICATIONS

"U.S. Appl. No. 13/574,738, Response filed Dec. 23, 2015 to Final Office Action dated Oct. 23, 2015", 14 pgs.

"Japanese Application Serial No. 2014-508505, Office Action dated Mar. 15, 2016", w/ English Translation, 9 pgs.

"U.S. Appl. No. 13/574,738, Applicant Interview Summary filed Mar. 22, 2016", 1 pg.

"U.S. Appl. No. 13/574,738, Notice of Allowance dated Oct. 13, 2016", 14 pgs.

"European Application Serial No. 12777556.7, Response filed Feb. 29, 2016", 16 pgs.

"Japanese Application Serial No. 2014-508505, Response filed Jun. 8, 2016 to Office Action dated Mar. 15, 2016", with English translation of claims, 11 pgs.

"Japanese Application Serial No. 2016-236535, Office Action dated Sep. 19, 2017", (English Translation), 5 pgs.

"European Application Serial No. 11737754.9, Extended European Search Report dated Feb. 13, 2018", 8 pgs.

"Japanese Application Serial No. 2016-236535, Response filed Feb. 21, 2018 to Office Action dated Sep. 19, 2017", w/English Claims, 7 pgs.

"European Application Serial No. 12777556.7, Communication Pursuant to Article 94(3) EPC dated Nov. 28, 2018", 4 pgs.

"European Application Serial No. 12777556.7, Response filed Feb. 19, 2019 to Communication Pursuant to Article 94(3) EPC dated Nov. 28, 2018", 12 pgs.

"European Application Serial No. 11737754.9, Response filed Sep. 3, 2018 to Extended European Search Report dated Feb. 13, 2018", 22 pgs.

\* cited by examiner

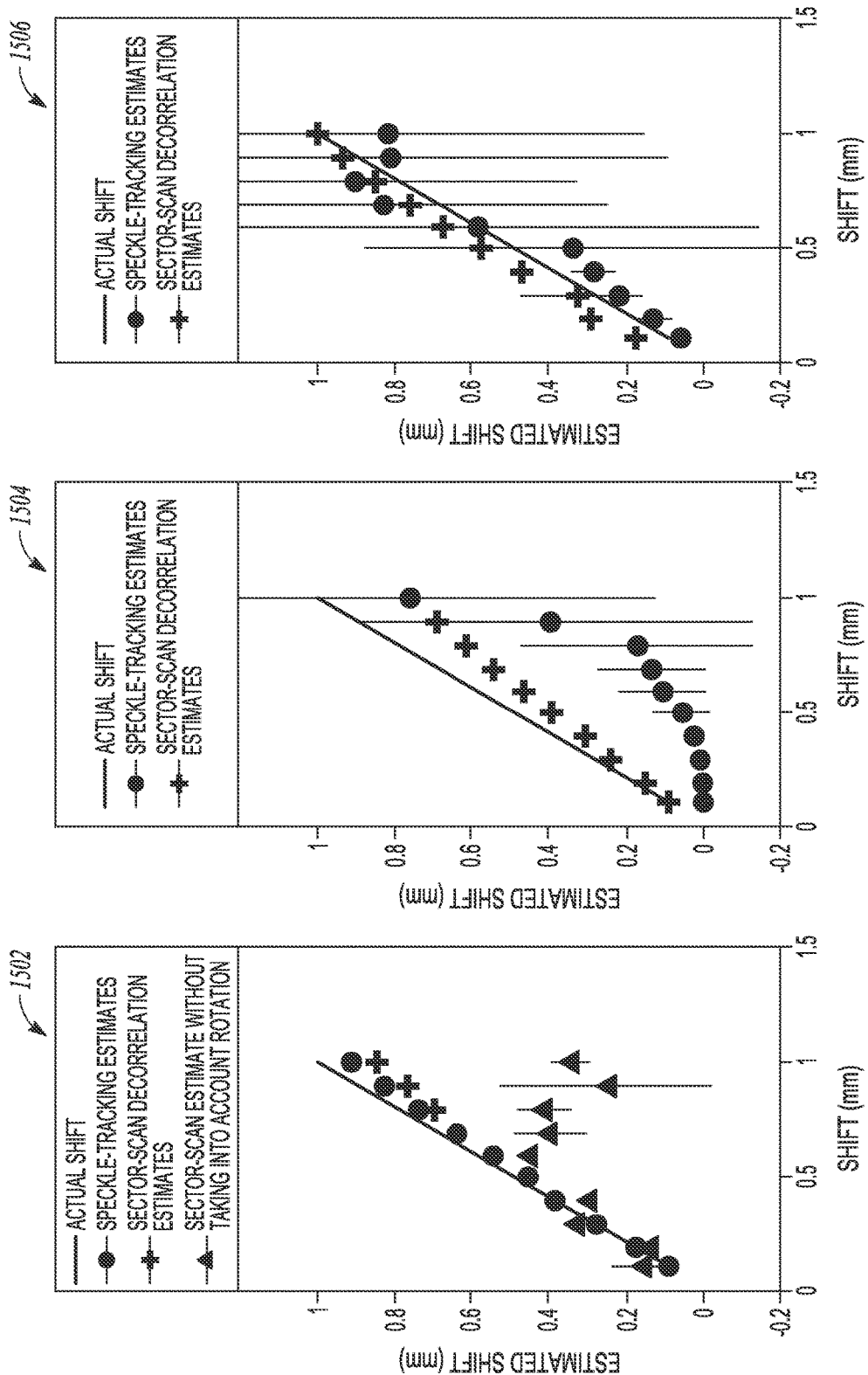

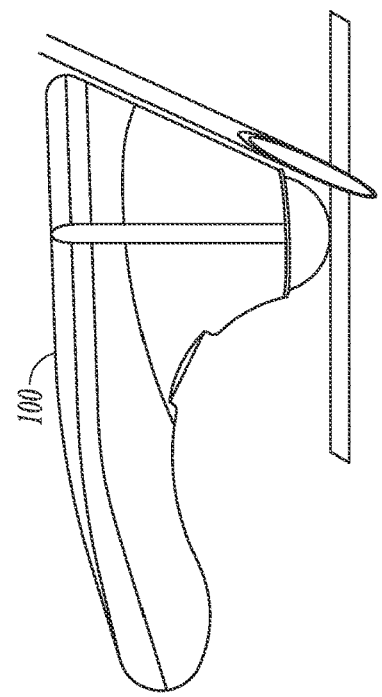
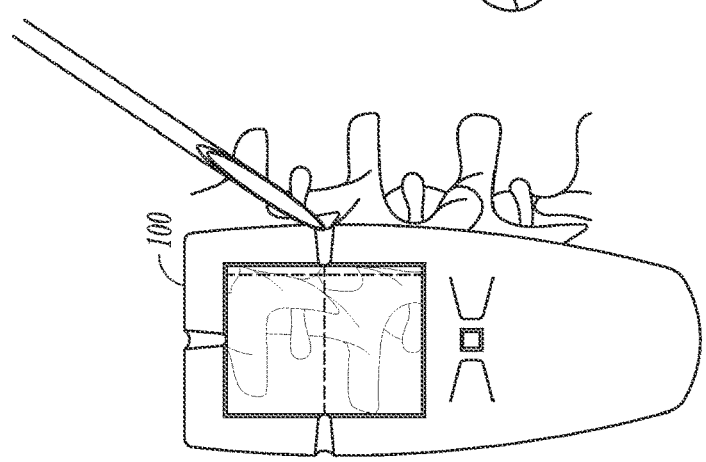
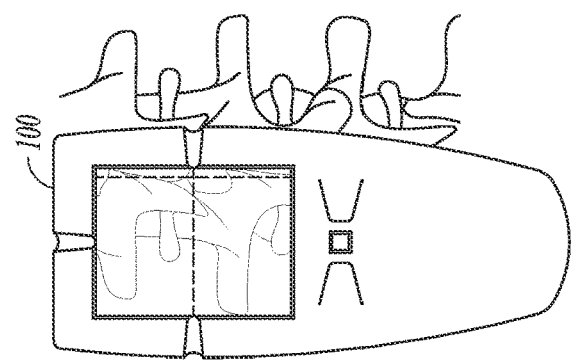

BONE SURFACE IMAGE RECONSTRUCTION USING ULTRASOUND

CLAIM OF PRIORITY

This application is a U.S. National Stage Filing under 35 U.S.C. § 371 from International Patent Application Serial No. PCT/US2012/034945, filed on Apr. 25, 2012, and published as WO 2012/148985 on Nov. 1, 2012, which claims the benefit of priority of U.S. Provisional Patent Application Ser. No. 61/479,072, filed on Apr. 26, 2011, titled "BONE SURFACE IMAGE RECONSTRUCTION USING ULTRASOUND"; U.S. Provisional Patent Application Ser. No. 61/547,175, filed on Oct. 14, 2011, titled "BONE SURFACE IMAGE RECONSTRUCTION USING ULTRASOUND"; U.S. Provisional Patent Application Ser. No. 61/569,685, filed on Dec. 12, 2011, titled "BONE SURFACE IMAGE RECONSTRUCTION USING ULTRASOUND"; and U.S. Provisional Patent Application Ser. No. 61/597,317, filed on Feb. 10, 2012, titled "BONE SURFACE IMAGE RECONSTRUCTION USING ULTRASOUND", the benefit of priority of each of which is claimed hereby, and each of which is incorporated by reference herein in its entirety.

BACKGROUND

Currently, 2D projection X-Ray or X-Ray computed tomography (CT) are frequently used as imaging modalities for bone imaging. However, ionizing radiation exposure to patients and caregivers from such medical imaging has increased dramatically in past decades (estimated at 600% increase since the 1980's). The cumulative effect of such radiation dosages has been linked to increased risk of cancer.

U.S. Pat. No. 6,641,537 (Morris et al.) mentions taking quantitative measurements of bone in vivo using ultrasound. U.S. Pat. No. 6,964,639 (Sela et al.) mentions mapping irregularities of bone using ultrasound. U.S. Pat. No. 6,106,464 (Bass et al.) mentions image-guided surgery in the brain. U.S. Pat. No. 7,806,823 (Sakai et al.) mentions an imaging technique for mechanical testing of bone.

Overview

Neuroaxial anesthesia blocks (e.g., epidural anesthesia or spinal anesthesia blocks) and related spinal anesthesia procedures are presently performed in approximately 18 million procedures per year in US hospitals. Numerous clinical indications for such procedures include anesthesia during pregnancy, chronic pain, or hip or knee replacement surgery.

In one approach, a "blind approach" (e.g., including no medical imaging guidance) can be used where needle insertion is performed after locating spinal bone landmarks using manual palpation. As a result, failure rates for such a "blind approach" have been historically cited as between 40%-80% in patient populations exhibiting landmarks that are absent, indistinct, or distorted. A significant and growing population segment exhibiting these characteristics is the obese, currently 33.9% of the total US population, with more than 50% of joint replacement patients included in this segment. In obese individuals, landmarks are not palpable due to thick overlaying layers of fat. Failures generally result in multiple needle sticks, which are correlated with poor health outcomes such as an increased risk of spinal headache or hematoma. In addition, other serious complications can occur from failed neuroaxial anesthesia including back pain (~30%), or vascular puncture (3.8%), as well as more severe complications including pleural puncture (1.1%), pneumothorax (0.5%), or paralysis (rare).

In another approach, fluoroscopy can be used to guide spinal needle placement with high success. However, the risk of ionizing radiation, in addition to high cost and lack of portability of fluoroscopy equipment, make fluoroscopy an unattractive option for a high-volume procedure.

In contrast to the "blind approach" or techniques involving fluoroscopy, ultrasonography can be a low-cost, non-ionizing, and portable solution for guidance to, or location of, anatomical features such as bone, such as used in a neuroaxial procedure. However, failure rates can still remain high, and the success of ultrasonic techniques has generally been highly dependent on user familiarity with ultrasonography. For example, interpretation of bone images with ultrasound at large scan depths can be challenging due to several factors including tissue attenuation or off-axis specular reflection artifacts. In addition, central neuroaxial procedures are generally performed multiple times per day by regional anesthesiologists. Thus, arranging access to the hospital scanner for such high-frequency procedures can be cumbersome or impossible in many hospital settings.

Bone fractures are common musculoskeletal injuries in the US, presently ranking second only behind sprains, and presently accounting for approximately 16.2 million injuries per year. The cost of bone fractures in the US is currently $29.2 B/yr, representing 90% of all musculoskeletal injury costs. While the elderly only represent <13% of the total US population, they are responsible for approximately 36% of all bone fractures with a fracture incidence rate of 9.7%. Additionally, the elderly are more likely to require hospital admissions, suffer limitations in their ability to perform daily activities, have significantly longer hospital stays, and have a higher mortality rate as a result of bone fractures.

Poor patient outcomes have been strongly correlated with treatment delays (especially in the elderly). For example, long waiting times are especially prevalent as a result of overcrowded emergency departments (ED) and lack of effective means to triage patients either off-site or on-site of injury.

Thus, the present inventors have recognized, among other things, that a low-cost, portable technology for triage of elderly patients at the site of injury or upon presentation to the ED could significantly reduce poor patient outcomes by reducing wait times, and could thus enable more rapid diagnoses and treatment decision making.

The present inventors also recognize that such specular reflections (e.g., predominantly specular reflections) can occur from bone-soft tissue interfaces or from soft tissue-soft tissue interfaces such as between boundaries of different organ types, blood vessel walls, or other targets, so such imaging techniques are applicable for detection of other interfaces or edges, such as for medical diagnostic purposes.

Similarly to imaging for neuroaxial anesthesia, X-Ray-based medical imaging, such as fixed X-Ray, fluoroscopy, or computed tomography (CT), is generally used for diagnosis of bone trauma. The use of X-Ray for patient triage in the ED to direct treatment has been proven effective for reducing waiting times in patients with fractures requiring surgery (e.g. hip fractures), thus reducing mortality and hospital stays. However, again, the lack of portability for X-Ray-based imaging inhibits its use in the ED for triage as time on the scanner must be arranged and the patient must be transported to the machine, which can be cumbersome in an overcrowded ED setting. Moreover, the lack of portability entirely precludes X-Ray use as a tool for rapid assessment and treatment at the site of injury such as during triage in mass trauma incidents. Radiation exposure due to medical imaging has increased approximately 600% since the 1980's, and recent studies have demonstrated that as many as 2% of all cancers are caused from medical imaging radiation exposure—equating to 11,000 additional deaths.

Ultrasound has been proposed for bone imaging in several applications, including spinal anesthesia, diagnosis of bone fractures, and guidance of orthopedic surgery. Ultrasound offers several benefits compared to X-Ray-based imaging including lack of ionizing radiation, superior portability, low cost, and real-time imaging. However, generally-available ultrasound apparatus and techniques have been engineered to image soft tissue, rather than bone, with the consequence that bone is imaged poorly due to several sources of image degradation such as off-axis reflections, reverberation effects, single channel saturation, or insufficient penetration depth.

The present inventors have, among other things, recognized the need for reduced-artifact images of bone with sharper delineation of bone surfaces from surrounding tissue in order to use ultrasound apparatus and techniques effectively as a safe, portable, inexpensive tool to assess and direct treatment for bone trauma patients or to provide detailed depictions of bone anatomy for needle or probe insertion guidance, without requiring ionizing radiation exposure to the patient or caregiver.

Various techniques and apparatus can be used for such imaging, such as ultrasound (US), which can provide real-time imaging along with equivalent or superior resolution as compared to imaging techniques involving ionizing radiation, and without the risk of such ionizing radiation. Generally-available US systems are engineered to image soft tissue rather than bone structures, with the consequence that bone is imaged poorly by such systems. For example, US images are often degraded by a number of noise sources including speckle noise, reverberations, or off-axis scattering, particularly when bone is present, making detailed visualization of the bone surface challenging. Thus, the efficacy of generally-available non-bone imaging ultrasound systems is limited and dependent on the user's familiarity and skill with ultrasonography.

The present inventors have developed techniques to mitigate or reduce off-axis-derived artifacts that can corrupt visualization of bone anatomy or one or more other tissue interfaces when such anatomy is to be imaged using an ultrasound diagnostic scanner. In an example, an intuitive display can be provided such as by estimating one or more of a location, shape, or orientation of the bone surface using such artifact-reduced echo data. For example, such echo data can be enhanced via probabilistic model-fitting of the echo data—or a parameterized version of the echo data—to a model.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 15A illustrates generally an illustrative example of an azimuthal shift motion estimation determined using various techniques, FIG. 15B illustrates generally an illustrative example of an elevation shift motion estimation determined using various techniques, and FIG. 15C illustrates generally a rotational shift estimation determined using various techniques.

FIGS. 21A through 21E illustrate generally a technique that can include identifying a needle insertion site and performing a needle insertion, such as for use in an epidural anesthesia procedure.

DETAILED DESCRIPTION

The present inventors have recognized that diagnostic ultrasound imaging can include tracking the position or orientation of one or more ultrasound transducers via an accelerometer, via an optical sensor, via using ultrasound motion tracking methods, or via one or more other techniques. Such techniques can be used to provide a position or orientation estimate for either a portion of the ultrasound apparatus (e.g., one or more transducer locations), or an estimate for the position of one or more anatomical features, such as bone, relative to the ultrasound apparatus, using information about a position, and orientation, or a change in orientation or position of the ultrasound apparatus. In an example, such a position or orientation determination can be performed on or within the ultrasound apparatus, or at least using one or more sensors or transducers located on or within the ultrasound apparatus.

In an example, apparatus or techniques can be used for diagnostic bone imaging via ultrasound. The present inventors have recognized, among other things, that grating lobes, side lobes, and lack of sufficiently tight focus in one or more dimensions can make generally-available medical ultrasound techniques or apparatus susceptible to off-axis reflection from bone leading. Such reflections can cause artifacts or poor image quality. For this reason, in generally-available diagnostic medical ultrasound imaging applications, bone imaging is generally avoided. Instead, X-Ray-based imaging modalities are generally used for such bone imaging.

The present inventors have developed techniques and apparatus for effective bone imaging using ultrasound, such as mitigating off-axis scattering-derived artifacts that can corrupt estimates of bone depth from echo data in existing generally-available ultrasound imaging. In an example, images can be constructed from echo data such as through rendering of one or more estimates of bone surface distance from the transducer rather than using beamforming, envelope-detection, and log-compression.

Figure 1:
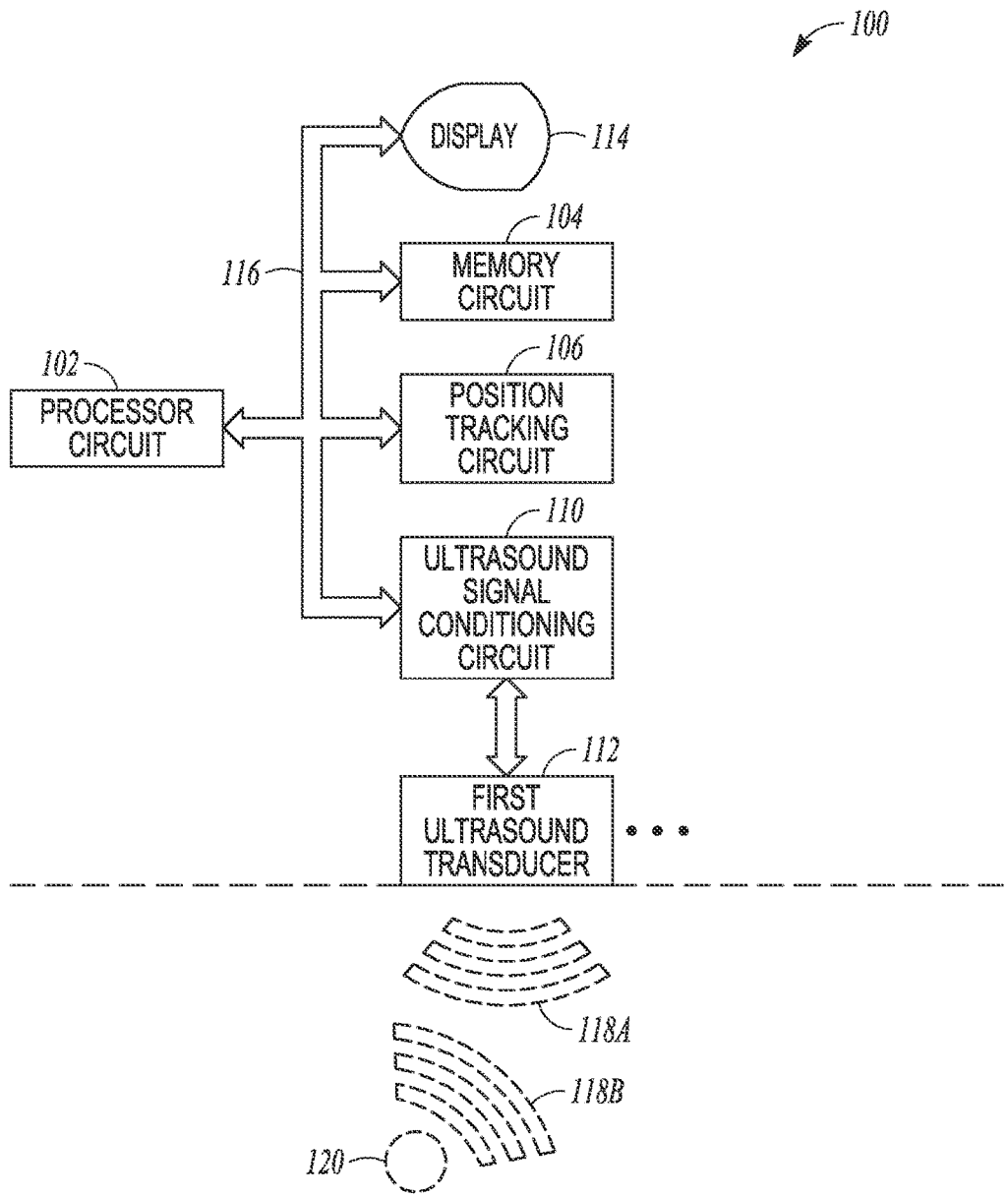
FIG. 1 illustrates generally an example of an apparatus, such as a hand-held apparatus, that can include an ultrasound transducer and a display.

FIG. 1 illustrates generally an example of an apparatus 100, such as a hand-held apparatus, that can include an ultrasound transducer 112 and a position tracking circuit 106. In the example of FIG. 1, one or more ultrasound transducers, such as the first ultrasound transducer 112, can generate ultrasonic energy 118A to be directed into a subject (e.g., insonifying a region of interest within the subject). Some of the ultrasonic energy 118A can be reflected by the target 120, such as providing reflected ultrasonic energy 118B. In an example, the ultrasonic transducer 112 can be included as a portion of an ultrasonic transducer array, and can be placed in contact with a surface (e.g., skin) of a patient.

In an example, the reflected ultrasonic energy 118B can be received by the first ultrasonic transducer 112, or by one or more other ultrasonic transducers. The first ultrasonic transducer 112 can be coupled to an ultrasonic signal conditioning circuit 110, such as coupled to a processor circuit 102 or a memory circuit 104 via a bus 116. The ultrasonic signal conditioning circuit 110 can include beam-forming circuitry or other processing circuitry. For example, the ultrasonic signal condition circuit can be configured to amplify, phase-shift, time-gate, filter, or otherwise condition received ultrasonic information (e.g., echo information), such as provided to the processor circuit 102.

For example, the receive path from each element in a transducer array, such as an array including the first ultrasonic transducer 112, can include one or more of a low noise amplifier, a main-stage amplifier, a band-pass or a low-pass filter, or an analog-to-digital converter. In an example, one or more signal conditioning steps can be performed digitally, such as using the processor circuit 102. The term processor is used to generically refer to digital circuitry that can be used to manipulate ultrasound information obtained from the ultrasound transducer 112. Such circuitry can include one or more of a field-programmable gate array (FPGA) or other programmable logic devices (PLDs), a microprocessor, a system-on-chip including one or more execution cores or other circuitry, a microcontroller, or one or more other circuits.

In an example, the apparatus 100 can be configured to obtain ultrasonic echo information corresponding to one or more planes perpendicular to the surface of an array of ultrasound transducers (e.g., to provide "B-mode" imaging information). In an example, the apparatus 100 can be configured to obtain information corresponding to one or more planes parallel to the surface of the array of ultrasound transducers (e.g., to provide a "C-mode" ultrasound image of loci in a plane parallel to the surface of the transducer array at a specified depth within the tissue of the subject).

In an example, the processor circuit 102 can be coupled to one or more processor readable media, such as the memory circuit 104, a disk, or one or more other memory technology or storage devices. In an example, a combination of one or more of the first ultrasonic transducer 112, the signal conditioning circuit 110, the processor circuit 102, the memory circuit 104, a display 114, or a user input can be included as a portion of a hand-held ultrasound imaging apparatus. The hand-held apparatus can include one or more piston-type transducers, such as configured to obtain depth information via reflections of ultrasonic energy from an echogenic target such as bone.

In an example, the processor circuit 102 (or one or more other processor circuits) can be communicatively coupled to one or more of a user input, or the display 114, such as via the bus 116. For example, the user input can include one or more of a keypad, a keyboard (e.g., located near or on a portion of ultrasound scanning assembly, or included as a portion of a workstation configured to present or manipulate ultrasound imaging information), a mouse, a touch-screen control, a rotary control (e.g., a knob or rotary encoder), or a soft-key aligned with a portion of the display 114, or including one or more other controls.

In an example, the processor circuit 102 can be configured to construct one or more composite images (e.g., a set of two-dimensional or three-dimensional representations of the location, shape, orientation, or depth of the target 120), such as using imaging information obtained using the first ultrasonic transducer 112 (or an array). The processor circuit 102 can present the constructed image to the user via the display 114, such as presenting an image including one or more features or indicia as shown in the examples below In an example, information can be obtained or sampled, the information indicative of ultrasonic energy reflected from the target 120 as the apparatus 100 is swept or moved across a range of locations. A composite can be constructed such as using information about the position of at least the transducer 112 of the hand-held apparatus 100 (or the entire apparatus), such as provided by the position tracking circuit 106, and information about reflected ultrasonic energy obtained by the ultrasonic transducer 112.

For example, the position tracking circuit can be coupled to one or more sensors, such as an accelerometer configured to sense acceleration in one or more axes, or an optical sensor. The position tracking circuit 106 can use one or more other techniques to determine a relative motion or absolute position of the apparatus 100 or one or more transducers included as a portion of the apparatus 100, such as using electromagnetic, magnetic, optical, or acoustic techniques, or a gyroscope, such as independently of the received ultrasound imaging information (e.g., without requiring motion tracking based on the position of imaged objects determined according to received ultrasonic information), or at least in part using received ultrasound information. For example, the position tracking circuit 106 can include using one or more processors configured to perform instructions, such as a method, including using information about transducer motion (e.g., either a detected transducer motion, or using a priori information about a transducer's position such as in the case of a mechanically-scanned transducer).

The apparatus 100 can include one or more transducers that can be mechanically scanned, such as to provide imaging information similar to the information provided by a two-dimensional array, but without requiring the user to manually reposition the apparatus 100 during a medical procedure. The apparatus 100 can be small and portable, such that a user (e.g., a physician or nurse) can easily transport it throughout healthcare facilities. The present inventors have also recognized other advantages to the apparatus 100, such as that it can provide imaging using non-ionizing energy, it can be safe, portable, hand-held, low cost, and can provide an apparatus or technique to align a location or insertion angle of a probe to reach a desired target depth or anatomical location.

Figure 2A:
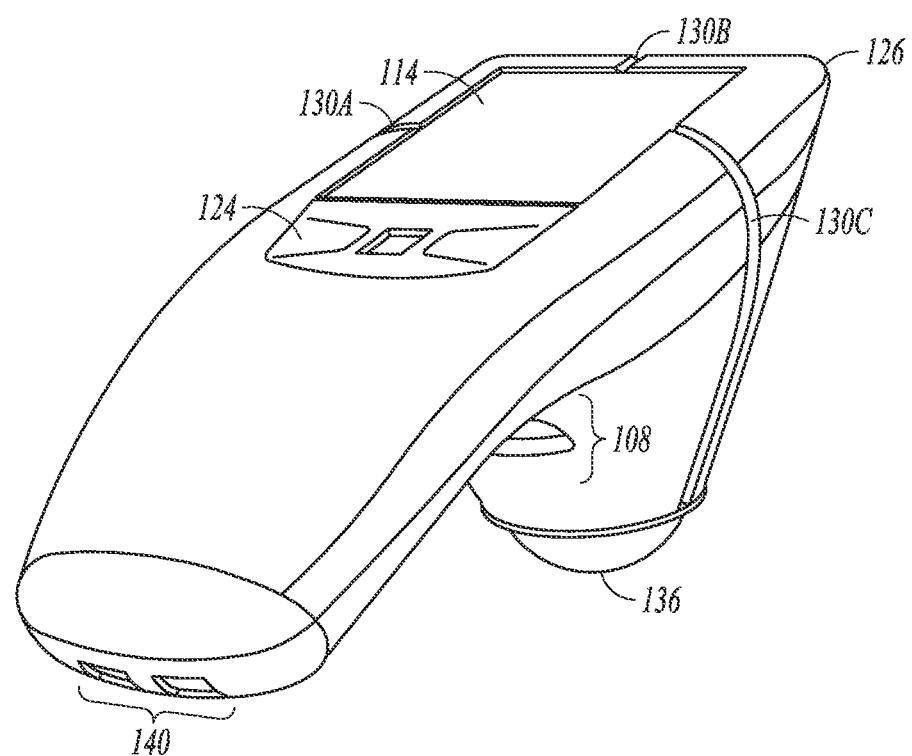
FIGS. 2A and 2B illustrate generally respective views of an illustrative example of an apparatus, such as a hand-held apparatus, that can include an ultrasound transducer and a display.
Figure 2B:
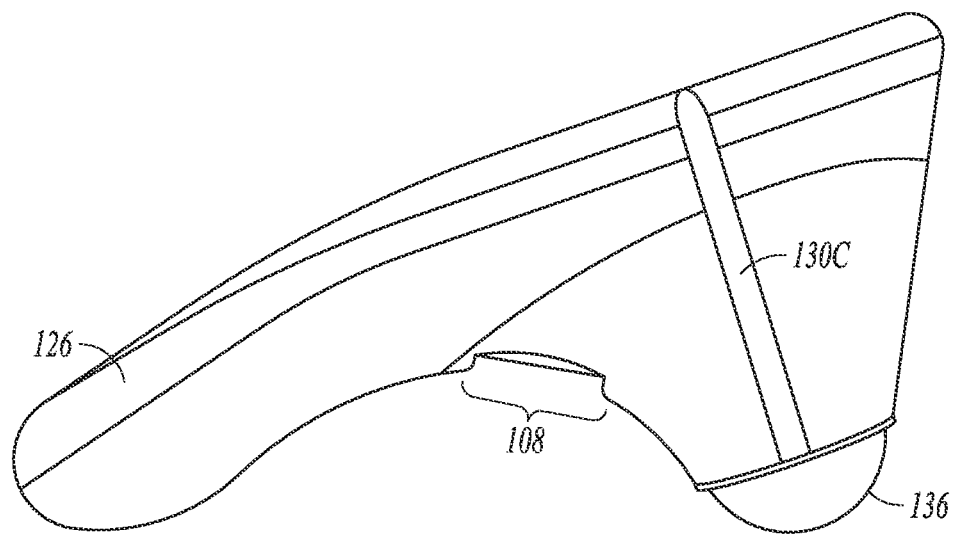

FIGS. 2A and 2B illustrate generally respective views of an illustrative example of an apparatus, such as a hand-held apparatus 200, that can include an ultrasound transducer 136 and a display 114, such as including one or more portions of the example of FIG. 1. The apparatus 200 can include one or more user inputs such as a first keypad 124, a trigger 108, or one or more other inputs (e.g., the display 114 may include a touch-screen or one or more soft-keys). The apparatus 200 can include one or more indicia to aid in alignment of the apparatus with a specified anatomical feature, location, or region. Such alignment indicia can include one or more displayed indicia presented on the display 114, or one or more fixed indicia located on a housing 126, such as a first indicium 130A, a second indicium 130B, or a third indicium 130C. One or more electrical ports can be included, such as for communication or recharging of a power source internal to the apparatus 200, such as including a port 140.

The present inventors have also recognized, among other things, that computational cost of use of a model-based image reconstruction can be a significant consideration when implementing such a technique on hand-held or portable apparatus. For example, such techniques (or other techniques discussed above) can be implemented on a cell-phone class "Open Multimedia Application Platform" (OMAP) microprocessor, such as available from Texas Instruments Inc., Dallas, Tex., USA, to provide a real-time display of a bone location, shape, or orientation, or other information on a hand-held apparatus. Such model-based techniques can be enabled at lower computational cost such as using parameterized versions of echo data (e.g. bone depth estimates) rather than operating on the echo data itself.

In an illustrative example, such as including one or more techniques described in examples above or below, such as including use of one or more transducers (e.g., 4 transducers and a 50 mm×90 mm sampled signal model with 1 mm spacing (i.e. a 4500×10400 signal model matrix)), a dot product calculation can be the most computationally intensive step and can involve approximately 94 million floating point operations (MFLOPS). In contrast, in another illustrative example, if data is parameterized by depth estimates across four channels, the computational expense reduces to 0.036 MFLOPS. For an OMAP3500 processor used in apparatus of FIGS. 2A and 2B, approximately 2400 MFLOPS/s of computational power can be available, thus respective frame rates for the two dot product steps can be achieved at 25.5 Hz using the full technique and 66.6 kHz using the parameterized technique. It is believed that drop-in replacement processors with significant increases in computational speed (e.g. >2× improvement) and marginal additional cost could enable even higher frame rates.

The present inventors have also recognized, among other things, that a ultrasonic transducer apparatus can use an increased excitation voltage (e.g. from ±32 volts (V) to +/−128 V or more), such as including an active protection circuit, in order to provide 12 dB gain from increased excitation voltage and 6 dB gain from active protection, respectively, for a total of 18 dB improvement in round-trip signal-to-noise ratio (SNR). In addition, coded excitation can be implemented to yield further SNR gains of as much as 22 dB without requiring additional transmit pulses.

An Illustrative Example that can Include One or More Large Transducers

Figure 3:
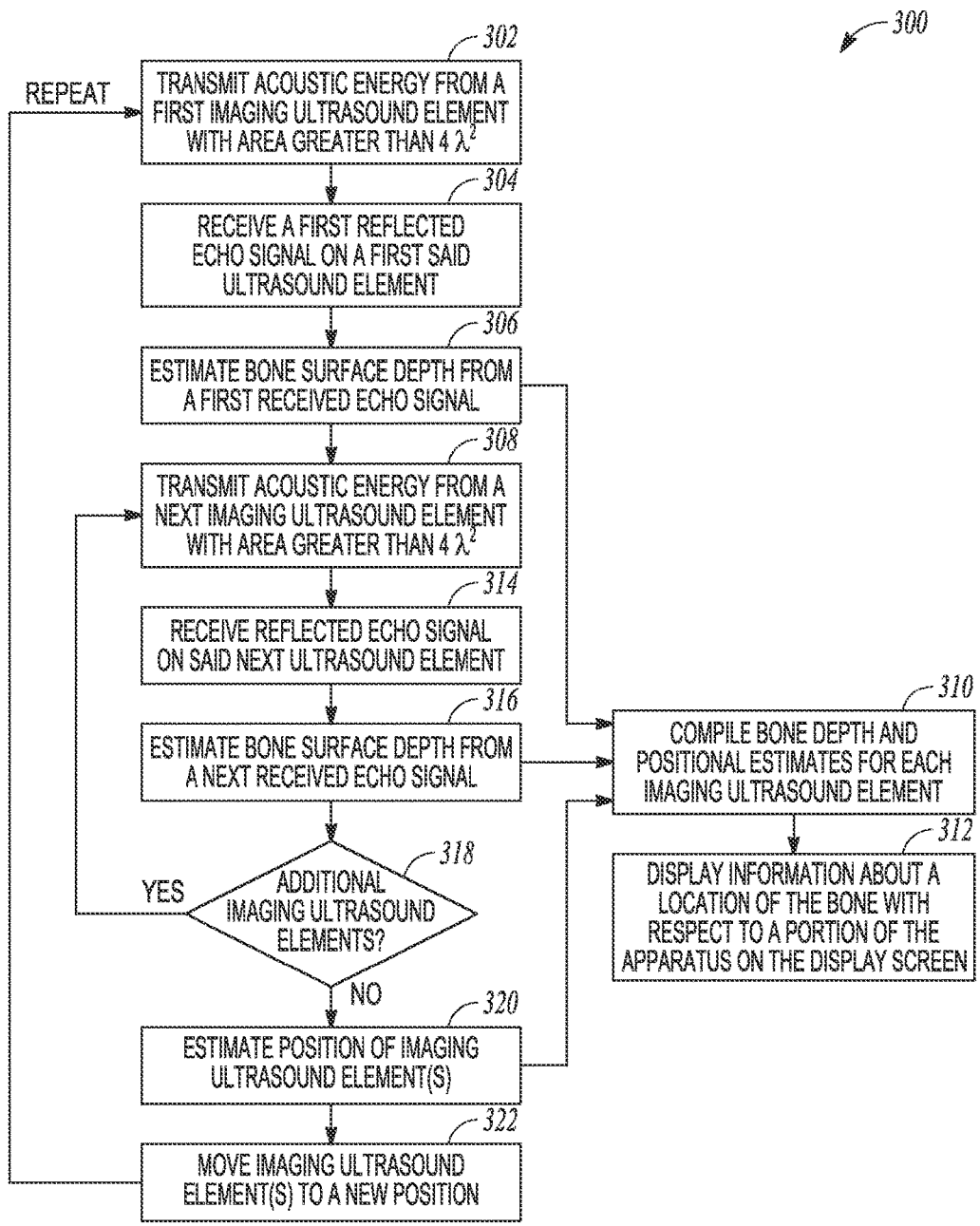
FIG. 3 illustrates generally an illustrative example of an ultrasound imaging technique.

FIG. 3 illustrates generally an illustrative example of an ultrasound imaging technique 300, such as can include apparatus and techniques that can involve independently operating, large, approximately circular ultrasound elements, such as including tracking one or more of the position or motion of a portion of the apparatus, and coupled to a processing circuit configured to one or more of compile echo data, compile position data, or provide image information for display of bone surfaces.

One or more transducer elements can be positioned arbitrarily along two spatial dimensions, such as for obtaining ultrasound information for rendering intuitive images of bone surfaces. Such a transducer can include any device that can convert electrical energy to ultrasound energy—or vice versa. Examples of such transducers can include piezoelectric-based transducers or electrostatic-based transducers, or one or more other transducer types.

In an example, the transducer element can be approximately circular or symmetrical such as having an area greater than $4\lambda^2$, where "$\lambda$" can represent the wavelength of the ultrasound pulse. Approximately circular can refer to a transducer element shape that is polygonal such as with an aspect ratio approximately equal to 1 (e.g., a transducer having an active surface including a dimension in length that is approximately the same as a dimension in width, in the plane of the transducer active surface). For example, the transducer element can include a square shape, or one or more other shapes such as having two or more axes of symmetry. The area criterion that the transducer area is greater than $4\lambda^2$ can be derived from a square aperture assumption. A lateral resolution can be approximately equal to $\lambda z/L$ where "L" can represent the length of the aperture.

For bone imaging, in an illustrative example, a desired maximum resolution of $5\lambda$ can be specified at a shallowest maximum focal depth, "z," of $10\lambda$. Such a constraint can thus provide that L should be greater than $2\lambda$ (e.g., $(10\lambda/5\lambda)*\lambda$) and therefore a corresponding transducer area can be $4\lambda^2$ or greater to meet the constraint. Transducer element lengths (e.g., an active surface of an element) are generally less than $2\lambda$ in existing ultrasound imaging systems. Thus, the present inventors have also recognized that transducer element sizes including a length or aperture having a dimension larger than $2\lambda$ (e.g., larger than existing generally-available ultrasound imaging systems) can be used such as to achieve a desired or specified resolution.

Linear arrays are used in generally-available diagnostic medical ultrasound imaging. In contrast, the present inventors have developed apparatus and techniques that can include the use of independently operating transducer elements (e.g., independently excited or receiving) including approximately circular elements. Independently operating elements that are approximately circular can be used to mitigate off-axis scattering artifacts that can corrupt bone images. Such mitigation or reduction can include 1) eliminating grating lobes or 2) providing resolution in the elevation and lateral dimensions that are similar (e.g., approximately equal), as opposed to generally-available 1-dimensional linear arrays that exhibit good azimuthal resolution, but poor elevational resolution.

In an example, to develop a 2D or 3D image reconstruction of a target (e.g., bone) with an element as described above, the element can be displaced (e.g., mechanically scanned) and the position of the element can be tracked before, during, or after such displacement. Echo data can be used, such as to provide bone depth estimates corresponding to specified element positions, such as compiled to provide a rendering of an image. The position or orientation of individual elements can be determined such as using the position or orientation of an imagine assembly housing such elements, such as along with element positions or orientations relative to the apparatus.

At 302, acoustic energy can be transmitted from an ultrasound transducer element. At 304, a first reflected echo can be received using the ultrasound transducer element. At 306, a bone surface depth can be estimated at least in part using the received echo. At 308, acoustic energy can be transmitted from a next ultrasound transducer (or the first ultrasound transducer can be repositioned either mechanically or via motion of the handheld assembly actuated by a user). At 314, a reflected echo can be received in response to the energy transmitted at 308. At 316, a bone surface depth can be estimate at least in part using the echo received at 314.

At 318, if there are additional ultrasound elements to be used, then the technique 300 can include respectively transmitting, receiving, and estimating as shown in 308, 314, and 316. At 320, a position of one or more ultrasound transducers can be estimated. If no additional ultrasound transducers are to be used, at 310, a bone depth estimate can be made and a position estimate can be made for one or more ultrasound transducers, and, at 312, information can be presented to a user about a location of the bone with respect to a portion of the imaging apparatus (e.g., the apparatus of FIG. 1, FIG. 2, or one or more other examples).

At 322, the one or more ultrasound elements can be moved to a new position. Displacement of an element can be achieved via mechanically sweeping the element inside the apparatus or moving the element manually and estimating displacement using one or more of position or orientation sensing methods. For example, tracking of transducer position to determine a position of the transducer beam can also include tracking orientation of the transducer, as both can affect the transducer beam.

In an example, independent motion estimates can be obtained from one or more sensors included in an ultrasound imaging assembly, such as via obtaining information from a 1, 2 or 3-axis accelerometer, a gyroscope, an optical motion sensor (e.g., as used in optical finger navigation, for example by Avago Technology—avagotech.com), amongst other motion sensing technologies.

In addition, or instead, motion of one or more of a transducer or the ultrasound imaging apparatus can be tracked using ultrasound echo data such as via template matching or decorrelation measurement. Such motion estimation can include aggregation of sensed information from one or more sensors, such as using information obtained from sensors having different sensing modalities (optical, acceleration, ultrasonic, or the like). For example, different motion estimates determined from different sensors can be combined in a statistical manner to produce a more robust (e.g., less ambiguous or less erroneous) position estimate as compared to an estimate derived from an individual sensing modality. A median or other central tendency of received estimates can be used. For example, a weighted average can be used where such a weighting can be derived from a measure of confidence or accuracy in an individual estimate (e.g. a ratio of a correlation "peak" to an RMS signal level).

Two or more motion sensors can be positioned at separate locations on the imaging apparatus. The sensor information obtained from the two sensors can be combined to calculate the position or rotational orientation of the apparatus. This can be used to calculate in turn, the positions of the transducers as the apparatus is rotated or translated. Using per-transducer position estimates, the information from the ultrasound echoes or bone depth estimates as the apparatus moves around the spine can be combined to produce an image on a display screen. Such an image can be persistent, such as updated as the apparatus is moved across the skin, such as to maintain a location of the image relative to one or more actual anatomical feature locations, or to form a composite image.

Figures 4A, 4B:
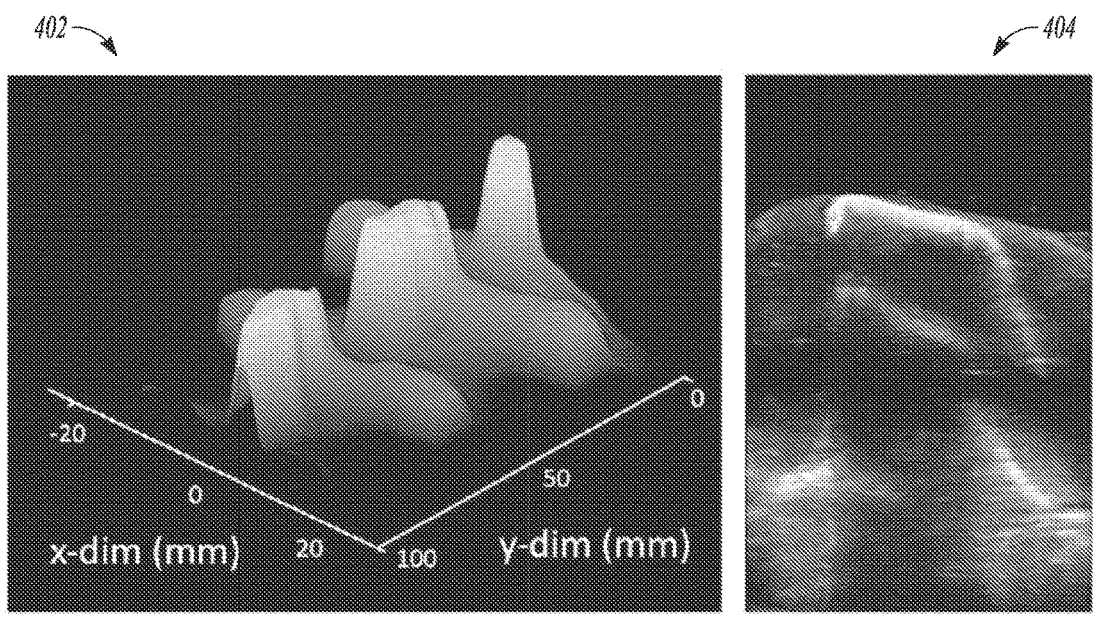
FIG. 4A illustrates generally an illustrative example of a three-dimensional representation of an ex vivo spine.
FIG. 4B illustrates a corresponding illustrative example of a B-mode ultrasound image.

FIG. 4A illustrates generally an illustrative example of a three-dimensional representation of an ex vivo spine 402, and FIG. 4B illustrates a corresponding illustrative example of a B-mode ultrasound image 404.

As an ultrasound imaging apparatus is translated across the surface (e.g., manually moved across the skin of a patient), a build up of a 3D bone surface can be determined, such as rendered on the display. Such an operating mode can produce an image equivalent to or mimicking one produced by a large array of transducers such as without the extra associated cost and complexity of such an array. Such a built-up display can be more intuitive than generally-available 3D echo-data rendering as such generally-available rendering contains speckle or other noise sources. In an example, surface samples (e.g., 3D information sampled via ultrasound) can be retired (e.g., omitted from the display or the modeling process) or can be reduced in brightness or significance after a specified duration of time (e.g., updating the display to incorporate temporally newer data and retire temporally older or "stale" data). The one or more ultrasound elements can include elements used for imaging, elements used for position sensing, or elements used for both.

An illustrative example of the techniques of FIG. 3 can include collecting echo data on 3 channels and translating the device with a motion stage of a 2D region of interest spanning approximately 5 cm×10 cm. For example, FIG. 4A includes 3D images obtained by processing echo data off-line using the imaging techniques described above. By comparison, FIG. 4B illustrates an ultrasound B-mode image of the same spine in a similar imaging environment obtained using the Ultrasonix RP (Ultrasonix, Richmond, BC, Canada) with a 128-element linear array operated at 6.67 MHz center frequency. The present inventors have recognized, among other things, that the 3D image obtained from a 4-channel device as shown in the illustrative example of FIG. 4A can be more intuitive to the user and can exhibit much lower levels of noise and artifacts as compared to the image obtained using the apparatus of FIG. 4B.

For purposes of modeling or discussion, bone surfaces can be referred to as specular reflecting surfaces. However, in practice, bone surfaces can exhibit characteristics of specular and diffuse reflection. For example, almost all of the incident ultrasound energy insonifying the bone is reflected, but the roughness can cause some energy to be reflected at a variety of angles, which is not strictly specular reflecting behavior. However, such a specularity assumption can still be valid as the reflection from bone much closer to specular in nature than reflections from soft tissues, which are much weaker reflectors, and which in general appear to have random directivity, as compared to bone. Thus, in the examples herein, ultrasound apparatus and techniques referring to imaging specular reflecting targets can be used to image targets that reflect the bulk of ultrasound energy directed at them, with some bulk directivity, but the targets can also include some diffusivity in their reflectiveness, reflecting some of the incident energy in a variety of directions.

Figure 5:
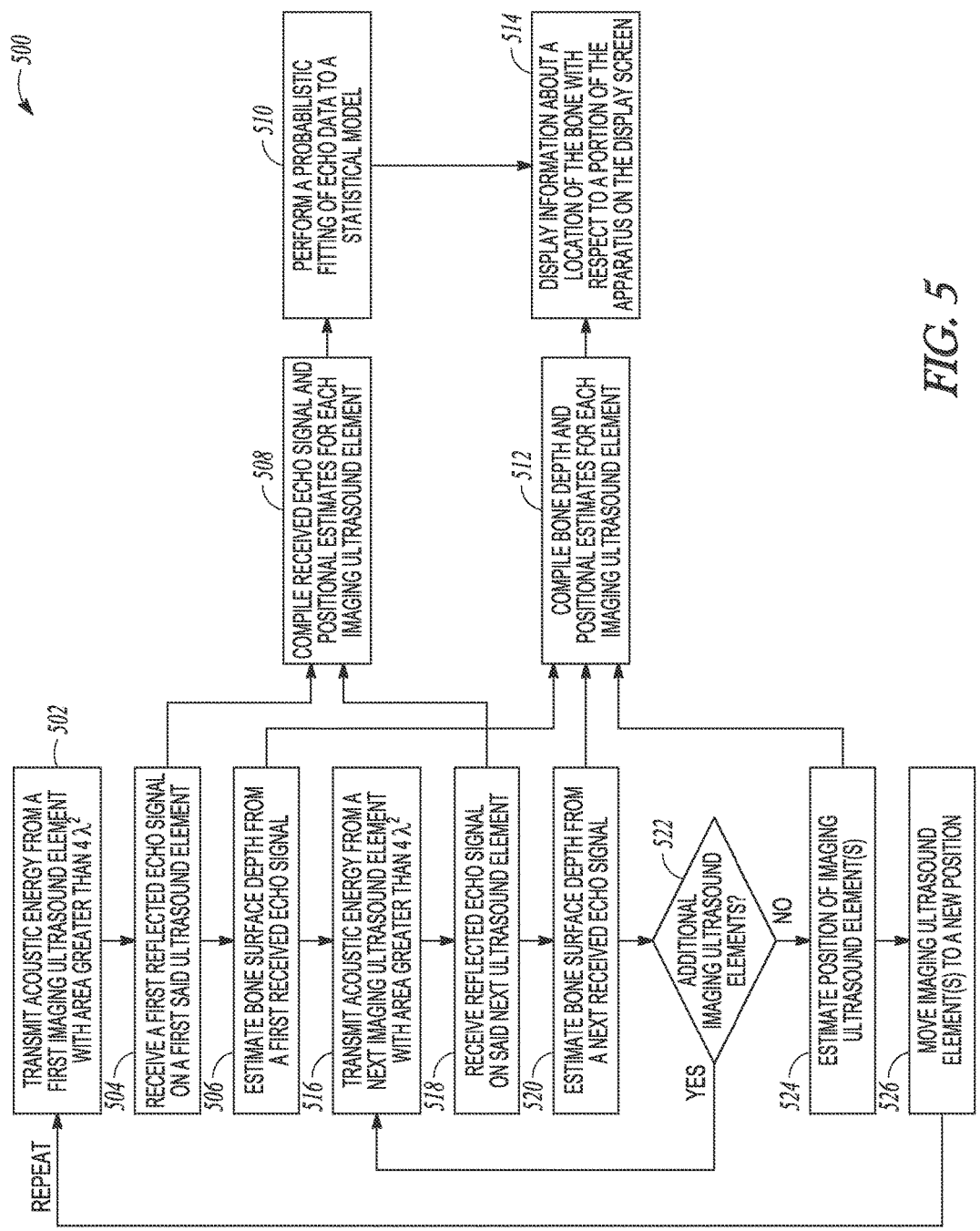
FIG. 5 illustrates generally an illustrative example of an ultrasound technique including using a model to estimate an anatomical target location, shape, or orientation.

FIG. 5 illustrates generally an illustrative example of an ultrasound technique 500 that can include using a model to estimate an anatomical target location, shape, or orientation. At 502, acoustic energy can be transmitted from an ultrasound transducer element. At 504, a first reflected echo can be received using the ultrasound transducer element. At 506, a bone surface depth can be estimated at least in part using the received echo. At 516, acoustic energy can be transmitted from a next ultrasound transducer (or the first ultrasound transducer can be repositioned either mechanically or via motion of the handheld assembly actuated by a user). At 518, a reflected echo can be received in response to the energy transmitted at 516. At 520, a bone surface depth can be estimate at least in part using the echo received at 518.

At 522, if there are additional ultrasound elements to be used, then the technique 500 can include respectively transmitting, receiving, and estimating as shown in 516, 518, and 520. At 524, a position of one or more ultrasound transducers can be estimated. At 526, the one or more ultrasound elements can be moved to a new position.

If no additional ultrasound transducers are to be used, at 508, a position estimate can be made for one or more ultrasound transducers, and, at 510, a probabilistic fitting of echo data can be made to a statistical model. At 512, bone depth information and position estimates can be compiled corresponding to one or more ultrasound elements. At 514, information can be presented to a user about a location of the bone with respect to a portion of the imaging apparatus (e.g., the apparatus of FIG. 1, FIG. 2, or one or more other examples).

An Illustrative Example that can Include an Array of Transducers

In another illustrative example, apparatus and techniques can include using a 2D grid of ultrasound elements spaced at less than about ½λ pitch, such as including approximately circular subapertures, such as including tracking one or more of the position or motion of a beam axis corresponding to one or more subaperture positions, and coupled to a processor circuit configured to one or more of compile echo data, compile position data, or provide image information for display of bone surfaces. In this illustrative example, mitigation of off-axis artifacts can be achieved such as using a 2D array with less than ½λ pitch such as to reduce or eliminate grating lobes. One or more transducer elements in the array can include approximately circular subapertures such as to provide reasonable resolution in both axes parallel to the transducer element face.

An Illustrative Example that can Include a Model-Fitting Technique

In another illustrative example, apparatus and techniques can include using the apparatus or techniques of the examples above or below, along with a bone surface location estimation determined such as by fitting the received echo data, or a parameters version of the received echo data, to a model.

The present inventors have developed apparatus and techniques for rendering of bone surfaces from received ultrasound data such as using ultrasound information acquired as described in the examples above. Rather than (or in addition to) estimating an on-axis bone depth to construct a bone surface display, the present inventors have also developed apparatus and techniques that can include a reconstruction method that estimates bone surface location, position, or orientation, such as by performing a fitting of echo data, or a parameterized version of the echo data, to a model. Such echo data can be obtained using one or more transducer elements, information about the one or more element positions, or using subaperture techniques.

A model-fitting scheme can be used to infer bone surface locations outside of the regions interrogated by the ultrasound beam. Such estimation techniques can be used in combination with a reduced repetition rate of ultrasound transmit/receive events as compared to generally-available B-mode imagine techniques, and thus such an estimation technique can provide a comparably higher frame update rate. Model-fitting techniques can provide bone surface location estimates with improved bias or variance as compared to generally-available image reconstruction techniques.

Echo data obtained such as using the apparatus or techniques shown above and below can be fit to a parametric model. Such a model can include an anatomical feature of interest, such as a portion of the spinal anatomy (e.g., a "candidate" target). Such a model can be used to estimate a relative position, orientation, or size of the feature with respect to the apparatus. For example, signal processing techniques, such as including statistical techniques, can be used to fit the received echo data to a parameter model according to specified criteria (e.g., to reduce, enhance, maximize, minimize, or otherwise meet a specified criterion or metric).

For example, a maximum likelihood estimate of the spinal anatomy positional parameters can be determined such as using a priori information concerning the spinal anatomy, the geometry or arrangement of acoustic sensors, or the noise statistics of the system, among other information. Other metrics can be used to yield estimates, and such metrics may be selected based on computational burden or noise immunity depending on system specifications such as frame rate, noise environment, power longevity or size for a hand-held assembly, etc.

A model-fitting approach can operate by fitting observed received echo data from one or more ultrasonic transmit-receive (TXIRX) events to a system model describing hypothetical (or previously-measured) received echoes from an array of different hypothetical bone surfaces (as discussed below). Such a model-based image reconstruction technique can use or can be seeded with RF echoes from some or all potential TX/RX element combinations for the array, such as to adjust (e.g., increase) the dimensionality or information content of the system model (e.g., to refine the model).

Defocused transducer elements can be used to give a large field of view such as using a relatively small number of transducer elements. For example, defocusing can be achieved by using a convex transducer surface or by using a defocusing lens. A defocusing lens can be designed using the Lensmaker's Equation. In an example, a convex lens surface can be used when the lens material provides a sound velocity greater than that of sound in tissue (e.g. a lens material such as including TPX® distributed by Westlake Plastics). In an example, a concave lens surface can be used when the lens material provides a sound velocity lesser than that of sound tissue (e.g. a lens material such as including RTV560 distributed by Momentive). Defocusing can reduce SNR as compared to using focused transducers, but this effect can be mitigated at least in part by the +35 dB relative brightness of bone echoes.

Following acquisition of echo data using all of, or a subset, of the full set of TX/RX combinations including an a transducer element array, image reconstruction can be performed, such as using a priori knowledge of spinal bone anatomy statistics and a signal model. Using such a model (e.g., a system model), an image of bone surfaces can be inferred from a probabilistic model-fitting approach instead of traditional beamforming.

In one approach, a linear observation model can be used, such as used elsewhere for sound navigation and ranging (SONAR) or radar image reconstruction. For example, "N" time samples can correspond to "M" received echoes for all or a subset of TX/RX combinations included in a transducer array, and "P" can represent a hypothetical collection of bone surfaces. A linear observation model can be represented by:

$$x = Sy \qquad (1)$$

where "x" of dim NM×1 can represent a vector of observed echo data from all TX/RX combinations on the array, and S of dim NM×P can represent a signal model matrix with each column representing a model of received echoes from a set of hypothetical bone surfaces (e.g., spinal bones) at particular positions in space.

A target vector, "y" of dim P×1 can correspond to actual weightings applied to each column of S. A priori information, such as the fact that individuals possess only one, unique spine, can be used to place constraints on the solution to EQN. (1). For example, only one non-zero entry in "y" can be possible in reality. Thus, instead of finding the precise weightings of all entries in "y", the problem can be described as determining which entry of "y" is non-zero (e.g., which spine location, shape, and orientation, as modeled by the columns of S, is the most likely given observed data, "x").

Various techniques can be used, such as determining which combination of the hypothetical spines has the highest likelihood given the presently-obtained echo data and a priori knowledge of the likelihood of various spine models. For example, the spine that has the highest weighting in the output can be determined as the spine representation to display, or can correspond to a specified spine representation to display. Such a determination can be made using a pseudoinverse operation, such as yielding the maximum likelihood solution given the model assumptions. However, once the mutual exclusivity of different spine instances is added to the model, the system can degenerate into a maximum normalized and weighted correlation (MNWC) approach. Such a MNWC approach can avoid problems associated with ill-conditioned inverse problems. The MNWC approach can include correlating the data set from the real spine with a set of hypothetical spines, normalized to remove effects due to some hypothetical spines' echoes being 'brighter' than others. For example, a weighting can be applied to a correlation, to take into account an a priori probability of a particular hypothetical spine, as some hypothetical spines can be more likely candidates than others, such as representing a maximum-likelihood technique.

Simulation can be used to assess the bias and variance of a model-based technique, such MNWC model-fitting technique above. The human spine geometry can be shifted laterally or in the depth dimension, or the amount of additive electrical noise can be varied. Simulated echo information from such scenarios can be obtained using FIELD II software. Bone surface estimates can be determined using the MNWC model-fitting approach, for a variety of lateral offsets, depths, and SNRs.

Probabilistic model-fitting technique can be enhanced in a number of ways. If the variable "x" is formed from parameterized, or pre-processed, echo data such as a vector of the estimated bone surface depths for each TX/RX event, computation complexity can be reduced as compared to using raw or unparameterized echo information.

An Illustrative Example that can Include a Sub-Unit Probability Estimation Technique Another enhancement can include modifying the system model to include a series of hypothetical spine sub-units rather than hypothetical whole spines. Such a sub-unit approach can provide estimates for spine anatomy as a combination of several different spine sub-units. The spine sub-units can include the spinal bone associated with a single vertebra, or other, smaller sub-units such as the spinous processes, or portions of the transverse processes that extend laterally from the spine, or one or more other sub-unit configurations. A sub-unit modeling approach can yield more complicated statistical properties, which can be used to increase the accuracy of the spine estimate. One such statistical property can include mutual exclusivity between sub-units that occupy the same three dimensional space. Another statistical property can include the spacing between adjacent spinal sub-units; for example, inter-vertebral distance has a statistical distribution.

An image representing a bone surface can be rendered via a superimposition or other combination of model-fitting and other bone surface location estimation techniques. For instance, bone surface location, shape, or orientation can be estimated from each echo individually, and then also from a model-fitting approach using a set of echo data, or using a parametric model of echo data. Color or other indicia can be used to identify image information corresponding to one or more construction techniques. For example, using different colors can help to illustrate which parts of a displayed image correspond to renderings of ultrasound echoes as compared to enhanced images inferred or otherwise constructed using a model-fitting technique.

In an example, estimation techniques can be employed that combine bone depth estimates acquired from received echoes on an individual basis with model-based iterative probabilistic statistical signal processing techniques. For example, one approach can include using a priori probability information to produce initial estimates of the spinal sub-units using a subset of the information available, such as using these estimates to produce an updated probability based on the estimates. Such updated probabilities information can be passed around the model as 'belief' messages, in order to re-compute the answer to the problem iteratively. Such techniques are generally referred to as "loopy belief propagation," and have been shown to converge in practical situations, such as producing better estimates at lower computational cost than other estimation techniques. In an example, such a technique can include:

(1) Assuming a spine model with a number of sub-units (e.g. different locations along the spinous process and transverse process) such as corresponding to different positions and orientations.

(2) Assuming that reflections from bone surfaces greatly reduce the amplitude of reflections from surfaces beneath bone (e.g., obstructed by the bone). Initial preprocessing of the received echo data can utilize the bone reflection properties to identify the most likely position of first bone reflection on each transmit/receive combination, reducing the size of the data set.

(3) Using the bone reflection data set and a priori probabilities for each sub-unit, providing an initial estimate for each sub-unit's probability or likelihood, using a weighted pseudoinverse for example. Such an estimate can be used to determine probabilities for each possible spinal sub-unit.

(4) Propagating a probability of a spinal sub-unit, in the loopy belief propagation technique, such as to modify the probability of other sub-units using, for example, a "sum-product" technique, or a linear or non-linear variation thereof. If a sub-unit at one position is likely, this can greatly reduce the likelihood of other sub-units that occupy some of the same space. Sub-units that are adjacent to the original sub-unit, such as forming a larger portion of continuous spinal bone from two or more sub-units, become more likely if the original sub-unit has a high probability. The original sub-unit can also affect the likelihood of similar sub-units that are separated in the direction of the spinal long axis by a typical vertebral separation distance. In these ways, the sub-unit's initial probability can be passed to the other sub-unit estimators as additional a priori information, which leads to sub-unit likelihood estimates with iteratively-improved accuracy. Collectively the additional probability information can improve signal-to-noise ratio for the spine estimate, such as if the model also takes into account electronic and other error sources such as speckle arising from overlying tissue.

In the examples above, the original echo data can be converted to bone surface depth estimates, before entering the loopy belief propagation stage. It is also possible to use information from the current step of the iterative spine sub-unit estimation to refine the estimation of the bone reflection positions, as the estimation of bone surface reflection position is itself a stochastic operation. For example, if a spinal sub-unit is postulated by the sub-unit iterative estimator with high likelihood, then bone surface positions that would likely arise from this sub-unit are more likely. Thus, probability information can propagate iteratively between the echo data domain and the bone surface domain. Loopy belief propagation can be used to exploit the statistical properties of spine topology and ultrasound imaging physics, giving improved accuracy in spine position detection, and enhanced robustness to noise sources.

Figure 6:
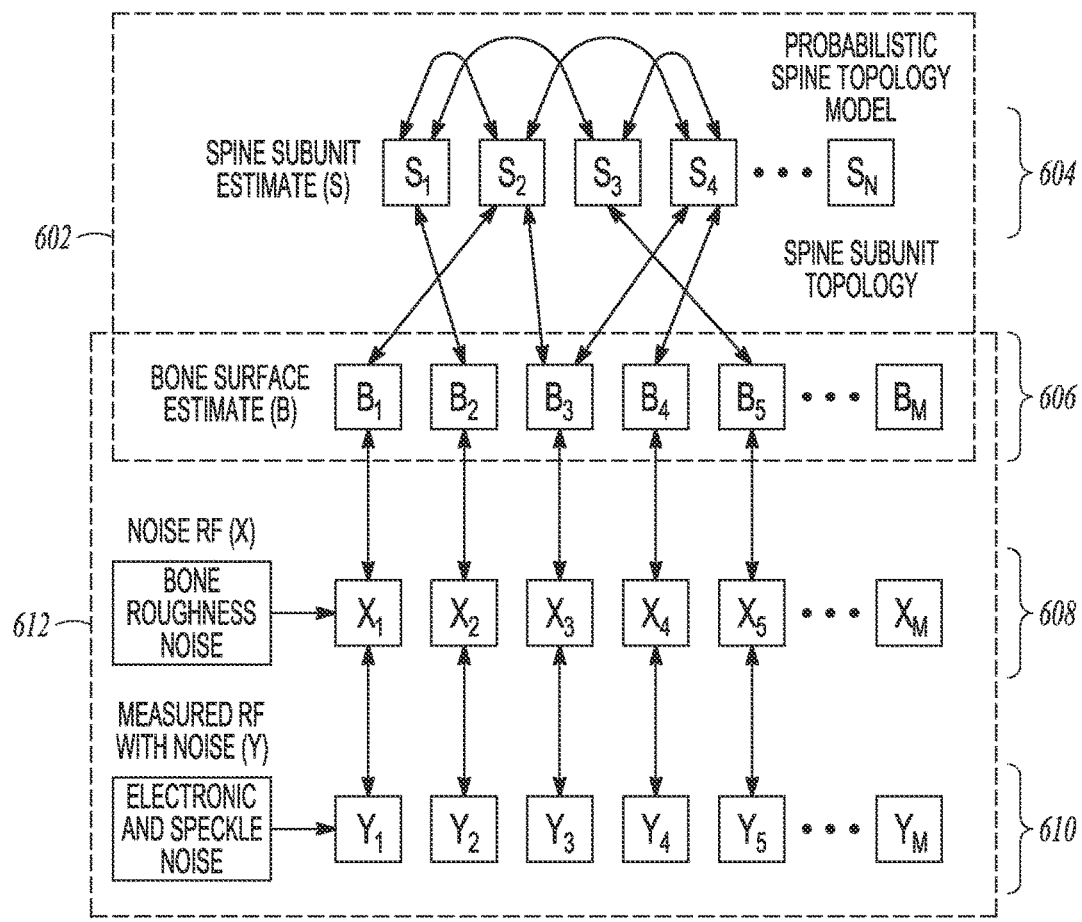
FIG. 6 illustrates generally an illustrative example of an ultrasound technique including using a model to estimate an anatomical target location, shape, or orientation.

FIG. 6 illustrates generally an illustrative example of an ultrasound technique 600 that can include using a model to estimate an anatomical target location, shape, or orientation. In the illustrative example of FIG. 6, at 604, "S" can represent the spine sub-unit probabilities. "S" can be a vector of the existence probabilities of various spine sub-units, which are hypothetical spine fragments, for example pieces of the spinous processes or transverse processes. The sub-units can form a library of parts that can be used to form any realistic spine. Therefore, this vector can provide a readout of the estimation technique.

At 606. "B" can represent bone surface position estimates. "B" can be a set of position estimates for the depth of bone surface at various positions in the X-Y plane parallel to the device surface applied to the skin. In an example, for an X-Y position, the bone surface estimate may consist of a Gaussian probability distribution, such as parameterized fully by a mean and variance. The set of bone position estimates, "B" can provide another readout of the estimation technique.

At 608, "X" can represent a noiseless RF signal that would be expected from a transmit-receive event located at a specified X-Y location, containing the echo data from a bone surface, if such a bone surface were present below the transducer. The noiseless RF echo can arise from the bone surfaces "B," and can also be modified by the bone roughness at the corresponding bone surface element, as indicated in FIG. 6.

At 610, "Y" can represent the measured RF with noise, such as obtained from a transmit-receive event at a specific location in the X-Y plane. This can be equivalent to the noiseless RF, "X," but with added electronic noise and speckle artifact. The electronic and speckle "noise" have statistical properties, shown as inputs to the Y variable.

The overall problem statement can be to estimate "S" or "B," given the measured RF signals and the properties of the system model comprising how spine sub-units in "S" map to bone surfaces in "B," and how these bone surfaces map to RF signals with noise effects. Such a problem can be solved, such as in one step, to produce a maximum likelihood estimate of "S" given "Y." However, such a single-step solution can be computationally inefficient, and some of the system model may involve non-linear mappings, making solution difficult. Instead, as shown in FIG. 6, the overall problem can be broken down into two sub-problems, providing a simpler and more computationally efficient iterative belief propagation approach:

(1) Bone Surface Position Estimation 612 can include the estimation of the bone surface positions given the received RF signals in "Y." Such an estimate can take into account the noise arising from electronic sources, speckle and bone roughness, plus information about the probability distribution of the spine sub-units in "S." The information about "S" can be combined with the information from the measured RF to produce enhanced estimates of the bone surfaces.

(2) Spine Sub-unit Probability Estimation 602 can include the estimation of the spine sub-unit probabilities "S," such as given the bone surface position estimates "B." A hypothetical spine sub-unit can include a reflecting bone surface at a location in space, therefore given "B" probabilities, "S" can be estimated, and given "S" probabilities, "B" can similarly be estimated.

A technique for iterating such an estimate can include:
1) Filling "S" with initial spine sub-unit probabilities based on the a priori probability of spine sub-unit existence in a general population of spines.
2) Using Y and the prior probabilities for the different spine sub-units in "S," estimating the position of bone surfaces "B," such as producing a mean and variance for bone surface element positions. This generally involves using knowledge of the transmit/receive system, statistical models of electronic or speckle noise, bone roughness, and using information about how the spine sub-units in S map to bone surfaces in B.
3) Using B and the prior probabilities of the spine sub-units, estimating "S" given the prior probabilities and "B." This generally includes taking into account how different bone surfaces arise from the spinal sub-units, and producing new probabilities for "S," such as incorporating information from the ultrasound echoes.
4) For the elements in "S," determining a new probability based on the existing probability (including information from received ultrasound echoes) and the probabilities of all other elements in "S." Such estimation of the new probability takes into account two features of the spine sub-unit model, first that a sub-unit at a specified location, if it exists, greatly reduces the likelihood of adjacent sub-units that overlap in 3D space. Secondly, if a sub-unit from one vertebra exists, then other sub-units are more likely to exist, including corresponding sub-units from the next and previous vertebrae, adjacent sub-units forming a connected piece of bone, and sub-units from the other symmetric side of the spine. Thus a probabilistic topological model of the spine can be used to refine the probability estimates of S. This operation may be a linear or nonlinear step.
5) A single iteration can be complete, and a new iteration can be started at (2), above, such as using the revised probability estimates for "S" and "B." Iteration can continue until changes in the estimates for S and B are relatively stable between iterations (e.g., meeting one or more specified criteria).

The iterative technique described above can use information about a probabilistic spine topology model that relates the probabilities of different spine sub-units to each other, and a spine sub-unit topology that relates different spine sub-units to the corresponding bone surfaces that are produced. It is believed possible to encode the probabilistic spine topology as one or more covariance matrices, describing the reinforcement, mutual exclusiveness and other probabilistic relations between the spine units. However, a procedural process can also be used to encode the probability dependence between sub-units, such as incorporating nonlinear elements. Nonlinearity can arise if the probabilistic spine topology incorporates both positive reinforcement elements and negative reinforcement elements.

The spine sub-unit topology can include a mapping between the different spine sub-units and the corresponding bone surface positions. This can be a deterministic bidirectional mapping. A single sub-unit corresponds to a location in space that can map to a series of bone surface elements with distinct positions in the X-Y plane and a depth in the Z dimension. However, each bone surface element in B can correspond to a probability distribution parameterized by a mean and variance. A marginal probability of a sub-unit can be updated using information about its existing probability and the probability information about its constituent bone surface elements in B. Similarly, given that a sub-unit can exist with a certain probability, its constituent bone surface element probability parameters can be updated, such as incorporating their expected positions given the sub-unit, and the sub-unit's probability of existence.

An output of the iterative technique can be a set of spinal sub-unit likelihoods, plus a set of estimates of bone surface positions. Thus, an image reconstruction for display can be formed using either one of these variables, or a combination of the two. Incorporation of the probabilistic spine topology can increase the accuracy and robustness of the final image formation as compared to generally-available B-mode imaging techniques.

Illustrative Examples that can Include Determining and Presenting a Two-Dimensional or Three-Dimensional Representation of a Target Apparatus and techniques can include rendering of bone surfaces, such as using portions of one or more of the examples discussed above or below, to provide a low-cost, portable, and intuitive-to-use apparatus that can provide higher success rates than a "blind approach" technique, and can do so at lower cost than using fluoroscopic or generally-available ultrasound techniques.

Figure 7A:
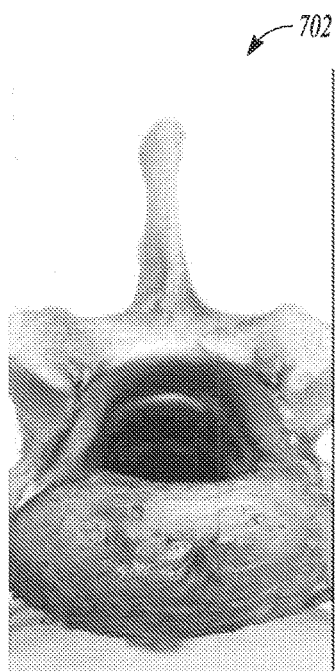
FIG. 7A illustrates generally an illustrative example of an animal spine.
Figure 7B:
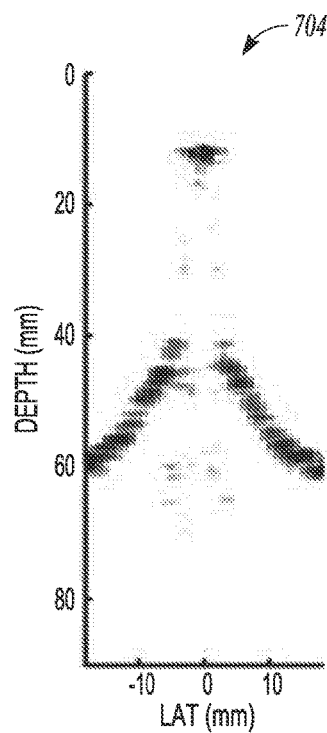
FIG. 7B illustrates generally an illustrative example of a two-dimensional representation of the spine of FIG. 7A.
Figure 7C:
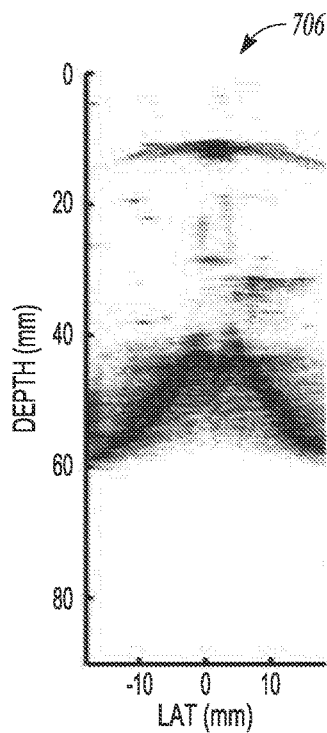
FIG. 7C illustrates generally a corresponding ultrasound image of the animal spine obtained using a commercially-available ultrasound system.

FIG. 7A illustrates generally an illustrative example of an animal spine 702, FIG. 7B illustrates generally an illustrative example of a two-dimensional representation 704 of the spine of FIG. 7A, and FIG. 7C illustrates generally a corresponding ultrasound image 706 of the animal spine obtained using a commercially-available ultrasound system.

In an illustrative example, an apparatus can be configured to provide pulse-echo ultrasound imaging such as using four channels and display data in real-time with automated bone depth detection, such as including a liquid-crystal display (LCD) touch-screen and Google Android user interface (or one or more other operating systems, interfaces, or displays). In an illustrative example, such as for comparison, such an apparatus (e.g., as shown in FIGS. 2A and 2B, or in other examples) and a commercially-available Ultrasonix RP system (Ultrasonix, Richmond, BC, Canada) can each be used to image an animal spine in a water tank across a 90 mm×50 mm 2D plane to produce 3D volume image data. Such experimental ex vivo imaging can be rendered in 2D or 3D, such as the two dimensional representation 704 included in the example of FIG. 7B. For example, images in FIG. 7B and FIG. 7C generally demonstrate good agreement with simulations depicted in the illustrative example of FIG. 9 where elimination of grating lobes using a piston transducer generally results in lower levels of imaging artifact.

Figure 8:
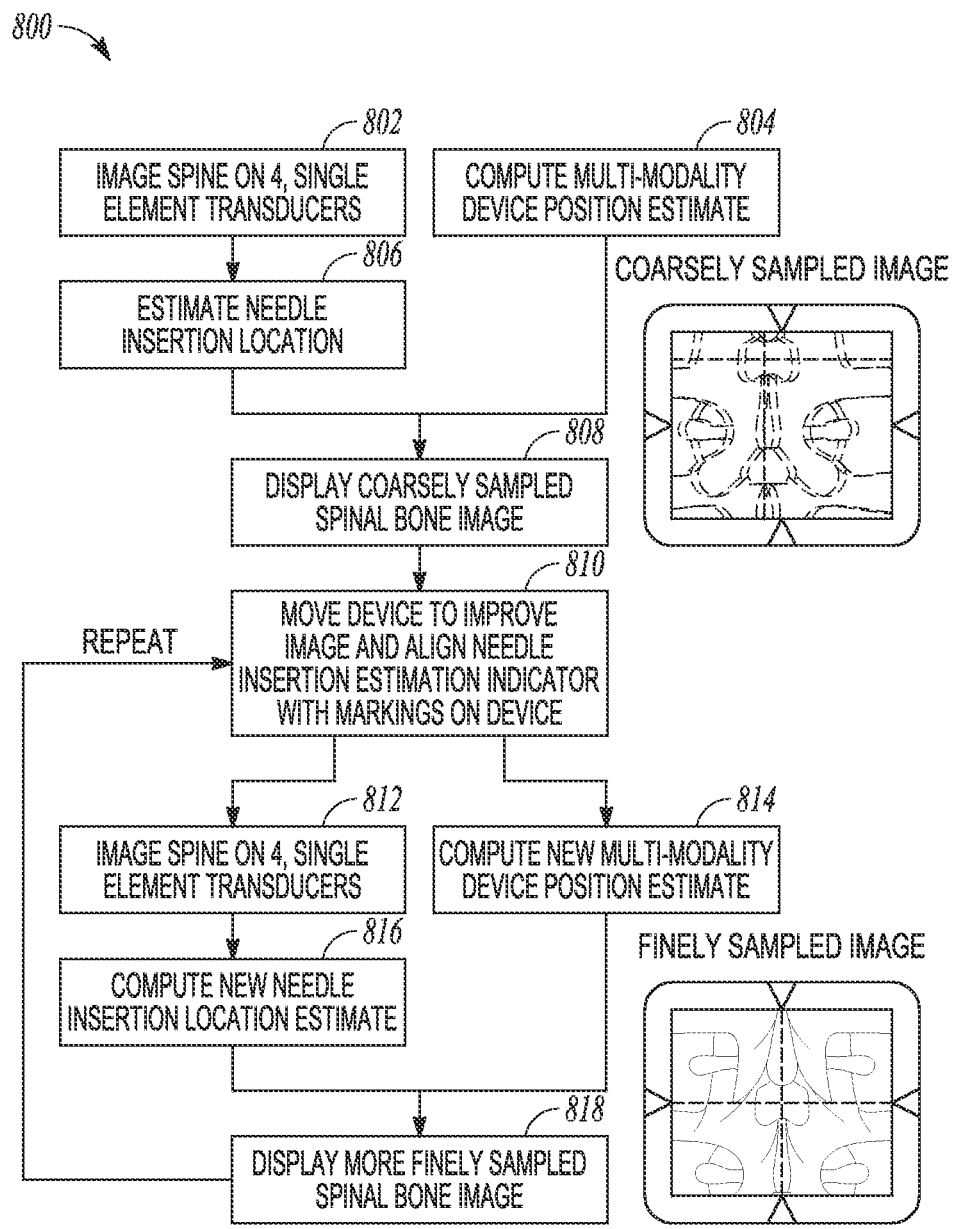
FIG. 8 illustrates generally an illustrative example of an ultrasound imaging technique.

FIG. 8 illustrates generally an illustrative example of an ultrasound imaging technique 800 that can be used to render an image of an anatomical target, such as bone, such as with automated determination and identification to a user of a needle insertion site (e.g., an interlaminar space).

In an example, images of spinal bone anatomy can be rendered using a low number of large (i.e. >2λ diameter), circular, single-element transducers such as shown in FIG. 8 at 802 or 812, and using a multi-modality device positional estimation technique shown in FIG. 8 at 804 or 814. The technique of FIG. 8 can provide several advantages over generally-available techniques. For example, the large, circular transducer elements can mitigate off-axis specular reflection artifacts that occur in generally-available ultrasound due to grating lobes and broad focus in the elevation dimension that are characteristic of linear array transducers. Also, the transducer geometry can, at least in part, mitigate artifacts that are prevalent from imaging of specular reflecting surfaces.

Additionally, the combination of single-element transducers with multi-modality position sensing technology can be lower cost than generally-available ultrasound apparatus, or lower cost and less complex than a mechanically-scanned transducer. In an example, an image display approach can be used to automatically determine and identify to a user an appropriate needle insertion site such as by fitting underlying ultrasound echo data to a spinal bone model. Such approaches help to simplify user interpretation of the underlying ultrasound data, and reduce or eliminate the need for specialized training in ultrasound image interpretation.

At 802, a predominantly specular target, such as a spine, can be imaged using four single-element ultrasonic transducers. At 804, a multi-modality position estimate can be determined (e.g., using information about received ultrasound energy, and information obtained from one or more other sensors or techniques, such as optical, magnetic, or acoustic information). At 808, an initial, coarsely sampled spinal bone image is shown such as after the first ultrasound A-lines are collected. At 810, the device (e.g., a handheld apparatus) can be moved to improve the image or align needle insertion indicia. As at 802, at 812, the spine can be imaged from the new position of the apparatus. At 814, a new multi-modality position estimate can be determined. At 816, one or more displayed indicia can be updated, such as an estimate of a needle insertion location.

For example, a user (e.g., a physician) can manipulate the device such as by translating it across the imaging area to improve image resolution until red needle insertion lines (e.g., a displayed indicium) are aligned with one or more device case markings (e.g., one or more fixed indicia), such as shown at 818, or using one or more other indicia. The user can then mark the patient's skin at locations adjacent to the device case markings, such as similarly to markings that can be provided in general practice for ultrasound guidance of central neuroaxial anesthesia.

Figure 9:
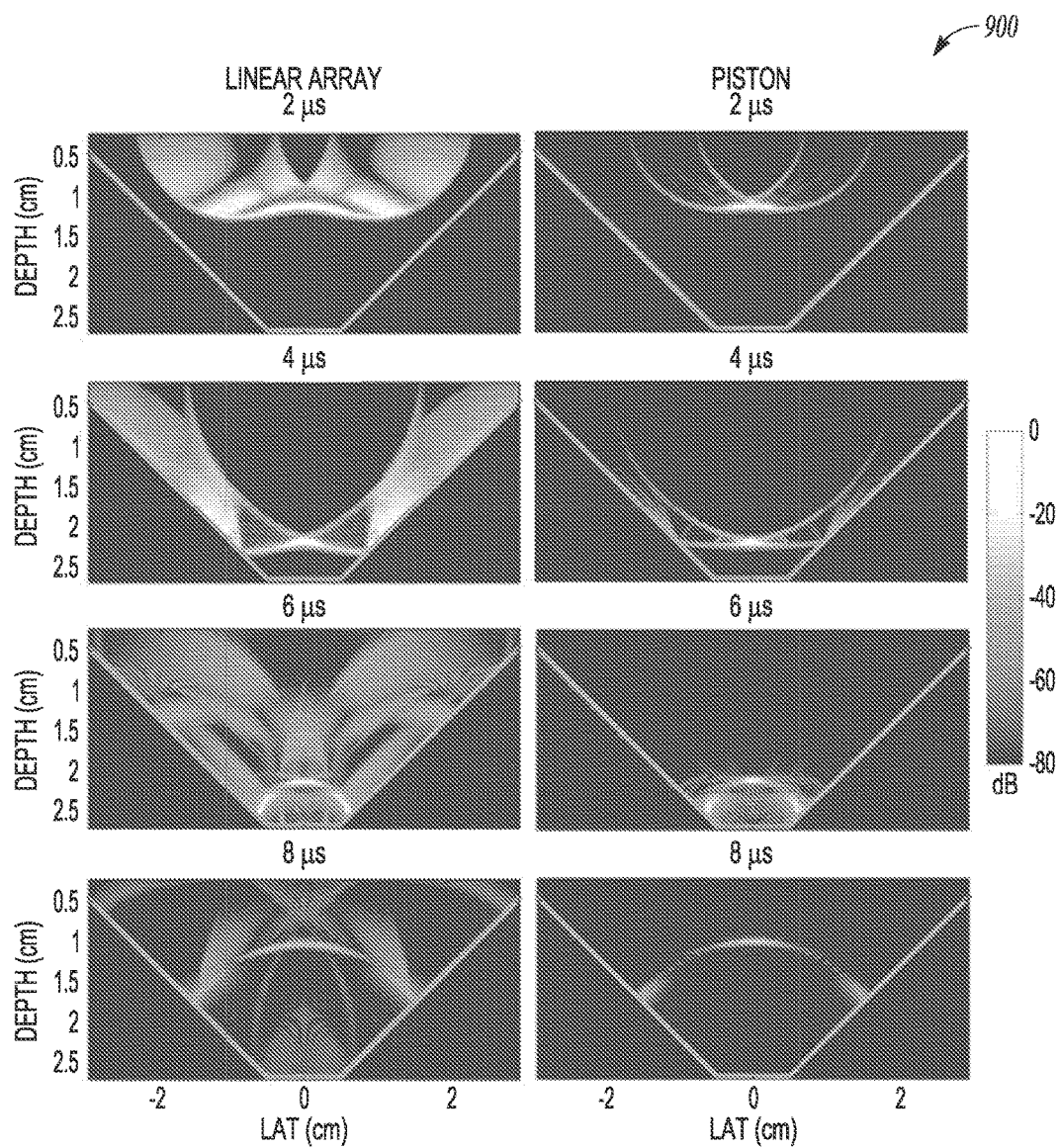
FIG. 9 illustrates generally an illustrative example of acoustic field amplitudes that can be obtained via simulation.

FIG. 9 illustrates generally an illustrative example of acoustic field amplitudes 900 that can be obtained via simulation. In an illustrative example, ultrasound imaging simulations can be performed using FIELD II software, such as to quantify off-axis reflection artifacts from a piston transducer having a ⅜" diameter, 5 MHz center frequency, with 5 cm focus, and as compared to a simulated Ultrasonix RP L14-5 linear array at 5 MHz center frequency, 300 micron pitch, and 5 cm focus, the array obtainable from Ultrasonix, Richmond, BC, Canada. For example, Specular reflection surfaces can be simulated such as by placing targets at uniformly spaced intervals along the simulated specular reflecting surface. On axis and off-axis surfaces can be simulated at varied imaging depths and angles.

For example, in off-axis specular reflection simulations, a focused piston transducer can suppress grating lobes and exhibit tighter focus in the elevation dimension. Consequently, use of such a piston geometry can provide less image artifact from off-axis specular reflections as compared with the linear array to yield an on-axis to off-axis reflection amplitude contrast improvement of more than 10 dB. In general, performance deteriorates with the linear array at higher frequencies where grating lobes can become more pronounced.

FIG. 9 illustrates generally an illustrative example of an effect of grating lobes from a linear array on the ratio of on-axis to off-axis reflection energy. Simulations can be performed in FIELD II as described above using the L14-5 simulated linear array operating at 10 MHz and the above-mentioned piston transducer operating at 10 MHz such as including both transducers focused at 3 cm. The first and second columns of images in FIG. 9 illustrate generally the propagation of the acoustic waves against on-axis and off-axis specular reflecting surfaces at various times.

For example, acoustic energy outside of the main lobe of the acoustic beam can be larger in the linear array than in the piston transducer due to grating lobes. Coherent reflections of grating lobe energy against off-axis specular surfaces can thus result in a significant increase off-axis reflection signal when using the linear array compared with the piston transducer. The present inventors have recognized that a high on-axis to off-axis reflection ratio is preferred for imaging as such a ratio is indicative of lower levels of image artifact. It is believed that grating lobes or insufficiently tight focus in the elevation dimension can be eliminated or reduced such as by using a piston transducer such as to image bone using ultrasound with substantially mitigated artifact as compared to using generally available linear arrays.

Figure 10:
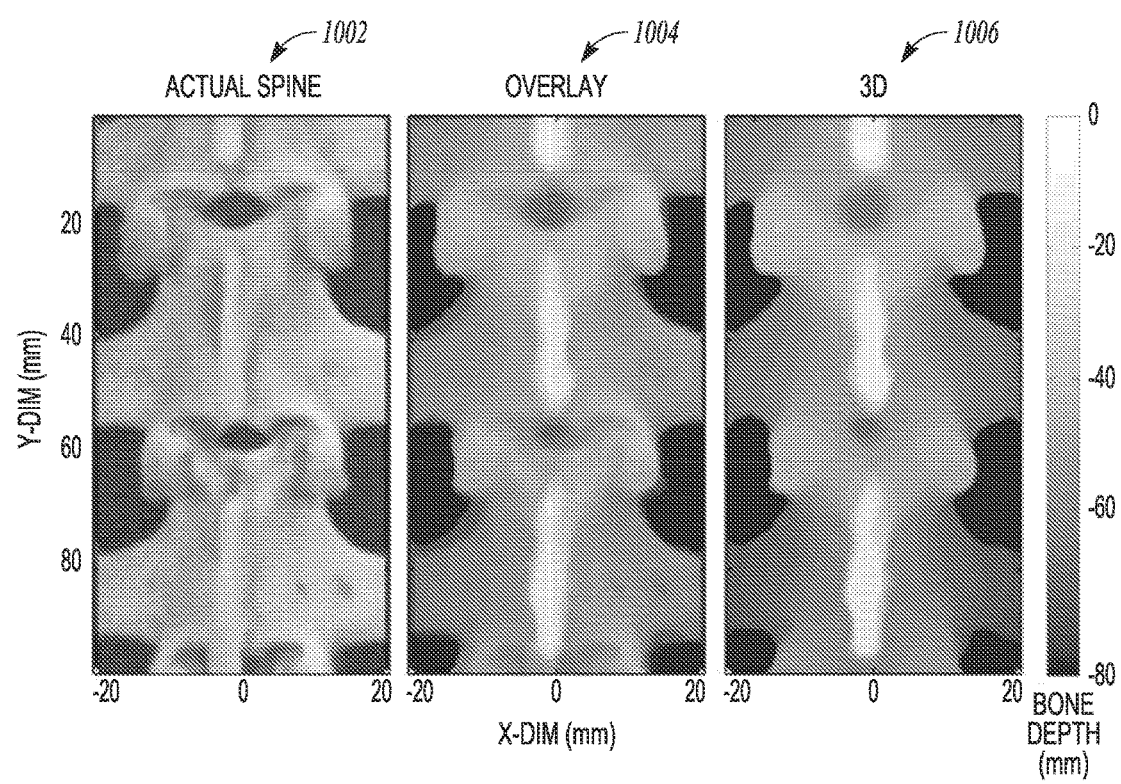
FIG. 10 illustrates generally an illustrative example of a photograph of an animal spine, a three-dimensional representation of the spine, and an overlay showing the animal spine photograph and the three-dimensional representation.

FIG. 10 illustrates generally an illustrative example of a photograph of an animal spine 1002, a three-dimensional representation of the spine 1006 (e.g., such as determined using one or more approaches above or below, such as can be presented to a user), and an overlay 1004 showing the animal spine photograph and the three-dimensional representation. The image rendering of FIG. 10C generally illustrates high correlation with an optical image of the spinal bone as shown in FIG. 10 OA, and an overlay of such a rendering and such an optical image is shown for comparison in FIG. 10B.

An Illustrative Example that can Include a Principal Harmonic Imaging Technique

Figure 11:
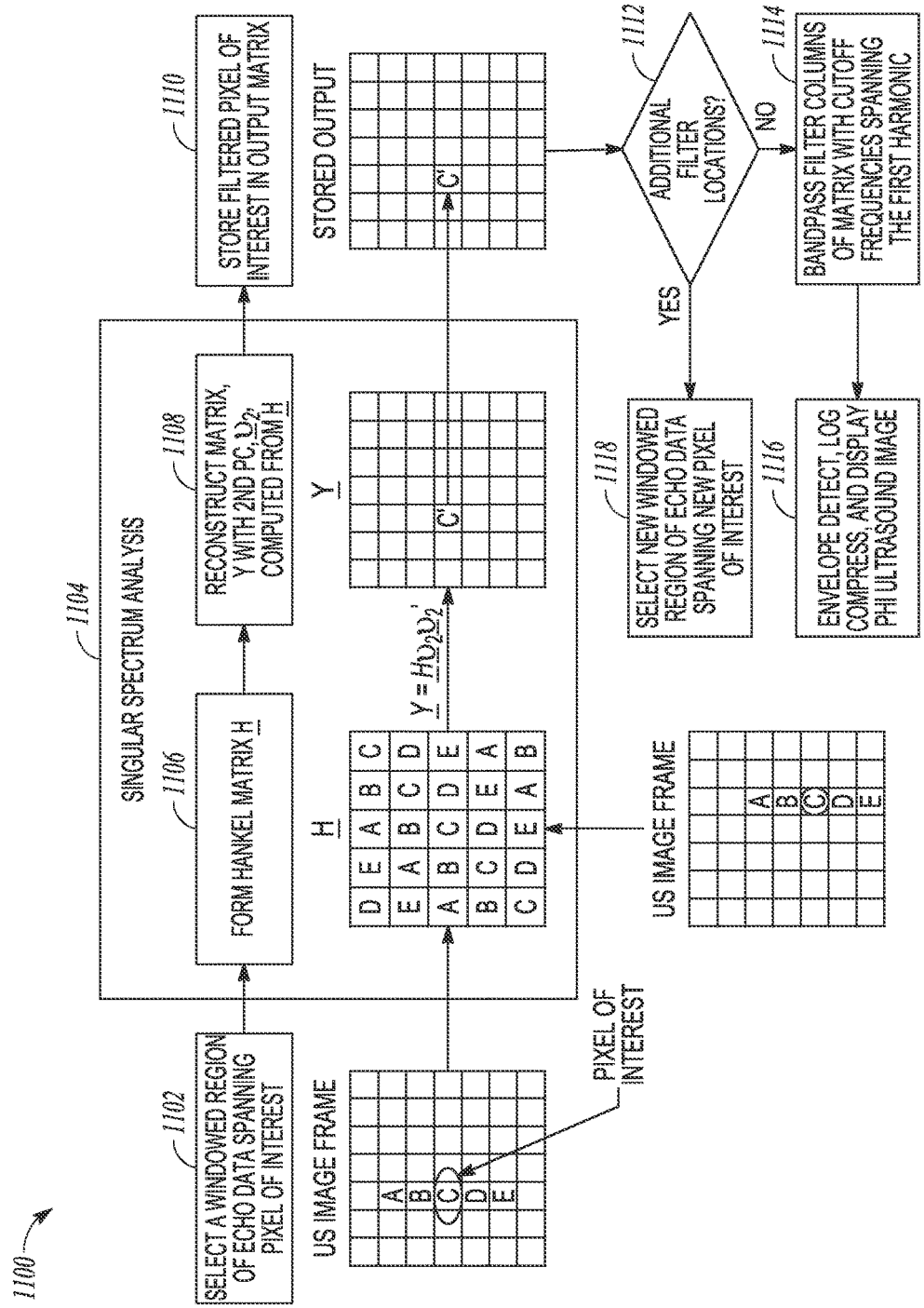
FIG. 11 illustrates generally an illustrative example of an ultrasound imaging technique.

FIG. 11 illustrates generally an illustrative example of an ultrasound imaging technique 1100 that can include rendering of bone surfaces from received ultrasound data using one or more portions of the techniques described in the examples above or below and that can include a technique for reconstructing ultrasound images that can be referred to as principal harmonic imaging (PHI).

In an example, a portable medical ultrasound-based bone imaging system with 3D imaging capabilities can be provided at lower cost (e.g., <$1K cost-of-goods-sold (COGS)) and in a more compact form than generally-available X-Ray or generally-available ultrasound equipment. Such a portable apparatus can be configured to perform techniques such as principal harmonic imaging (PHI). The present inventors have recognized, among other things, that PHI can, at least in part, reduce or suppress image artifacts, improve image resolution, or enhance delineation of bone surfaces from surrounding tissue and noise as compared with generally-available ultrasound imaging at the fundamental frequency.

Apparatus such as configured to provide bone surface imaging using a PHI technique could shift clinical practice and assist in assessment of bone trauma, such as in ED triage upon patient arrival. For example, by addressing the limitations of X-Ray-based imaging and generally-available medical ultrasound, the present inventors have also recognized that the present invention could increase the use and efficacy of medical imaging for triage of patients with bone trauma either at the site of injury or immediately upon presentation to the ED. Triage of patients with bone trauma has been shown to decrease waiting times, which in turn, improves patient recovery times, decreases hospital stays, and decreases mortality rates. Because the elderly are more likely to fracture bones and more likely to require invasive treatment as a result of fracture, the elderly segment of the population could benefit most from triage using portable, low-cost bone surface imagine apparatus and techniques.

In an example, principal harmonic imaging (PHI) imaging can be used to reconstruct ultrasound images. Such a PHI reconstruction technique can be implemented to render ultrasound images, such as including apparatus, such as a hand-held apparatus, configured to one or more of:

(1) collect an image frame of complex echo data;

(2) select a windowed region of echo data spanning a half of a wavelength such as 1102;

(3) perform singular spectrum analysis on the windowed region of echo data to obtain principal components (PCs) at 1104, including forming a Hankel matrix at 1106;

(4) project original data onto the 2nd PC (e.g. a most energetic PC describing signal outside the fundamental band at 1108;

(5) store the filtered pixel of interest at 1110;

(6) move the window to a new pixel of interest at 1118;

(7) repeat (1) through (6) and compile filtered outputs from (4), such as if additional filter locations exist at 1112;

(8) bandpass filter an output of (7) at the 1st harmonic, such as at 1114; and (9) envelope detect, log compress, and display a PHI image, such as at 1116.

An illustrative example of at least a portion of such a PHI technique is illustrated generally in FIG. 11. In an illustrative example, PHI can be used for 2D or 3D image reconstruction of a target (e.g., bone) as described in the examples above.

As an example, PHI can be applied to received echo data, such as the received echo data, to improve a position estimate of a target, such as a bone surface. For example, PHI filtering of the data can take place upon receiving the echo data on an ultrasound transducer, such as prior to estimating a bone depth or other information (e.g., one or more of a location, shape, or orientation). The present inventors have also recognized, among other things, that 2D ultrasound images can be rendered using PHI as a replacement for tissue harmonic imaging (THI). For example, PHI can be used to image bone or any other soft tissue anatomy such as heart, blood vessel, breast, liver, kidney, for example.

In an example, real or complex echo data can be used with PHI, and a windowed region of echo data can range any number of samples >1. In an example, singular spectrum analysis (SSA) can be performed as a portion of PHI, such as where a Hankel matrix is formed from a windowed region of echo data. The Hankel matrix can be mean reduced, and PCs can be computed from the mean-reduced Hankel matrix. A Hankel matrix can represent a matrix with constant skew diagonals. In an example, PCs can be computed via a singular value decomposition (SVD) of the Hankel matrix, an eigenvalue decomposition of the covariance or autocorrelation matrix of the mean-reduced Hankel matrix, or using one or more other techniques of computing the PCs of the mean-reduced Hankel matrix.

In an example, any number of pixels of interest from any number of echo samples can be used in PHI. For example, the original data can be projected onto any number of PCs. In an example, only the 2nd PC is retained as it is most likely to describe energy in the 1st harmonic when using a window length of a half of a wavelength. Reconstruction using the second principal component can be achieved such as using the relation:

$$Y = Hv_2 v'_2 \quad (2)$$

where H can represent the Hankel matrix, $v_2$ can represent the $2^{nd}$ PC vector, and Y can represent the reconstructed Hankel matrix obtained such as via filtering the $2^{nd}$ PC. In an example, PCs can be determined from a mean reduced Hankel matrix, and thus, the mean vector can be determined such as by taking the mean of columns in H and adding such means to each row in Y after determining Y via equation (2).

In an example, PCs may be selected adaptively from characteristics of the PCs such as the singular value spectrum properties or frequency properties of the PCs. For example, adaptive selection of PCs can include: the original data is projected onto all PCs that include frequency content in the 1st harmonic band above a specified threshold value. An output matrix can be formed, such as including elements determined using information from one or more reconstructed matrices, Y, such as corresponding to one or more pixels of interest in an image frame to be displayed. In an example, any form of bandpass filter can be used such as a filter spanning the fundamental frequency, 1st harmonic, or any combination of frequencies, such as applied to the output matrix (e.g., applied to one or more columns of the output matrix). For example, such bandpass (or other) filtering can be applied to the output matrix and then such a filtered output can be envelope detected, log-compressed, or otherwise conditioned such as for display to a user.

An image display method can be used to render an ultrasound image from echo data processed with the PHI technique. For example, PHI processed echo data can be envelope detected such as via computing the absolute value of the complex representation of such echo data, then log compressing the envelope-detected data, such as for display using a linear or non-linear gray scale mapping.

PHI can be compared to tissue harmonic imaging (THI); however, PHI can use a principal component analysis (PCA) technique to separate signal components at the harmonic frequencies. PHI exhibits advantages over THI that can include: signal components with overlapping frequencies can be separated (e.g., information corresponding to tissue can be separated from information corresponding to bone structure), in-band noise can be separated from signal, and the PHI technique can be adaptive to local spatial variations in the data. Thus, PHI can provide similar resolution improvements as can be provided by THI, such as compared with imaging at the fundamental frequency, but PHI can provide better reverberation reduction, sharper contrast of bone structures, or lower noise than THI or imaging at the fundamental frequency.

In an example, in addition to using PHI, mechanically scanned, circular, single element transducers with large diameter (i.e. >2 wavelengths) can be used. In an illustrative example, PHI can be used on received echo data from any transducer geometry including, for example, a linear array, a 1.5D array, a 1.75D array, a 2D array, an annular array, or one or more other arrays.

Ultrasound targets such as bone can be imaged using PHI operating on received echo data such as obtained from large, approximately circular transducers as described in examples. As discussed above, such single element transducers can mitigate various artifacts in bone imaging. While 2D arrays with <½ wavelength pitch would also mitigate off-axis reflection artifacts, such systems can be expensive and are generally not capable of being implemented in hand-held apparatus. In contrast, use of relatively large transducers can be performed in combination with one or more of multi-modality position estimation and PHI, such as in a hand-held assembly.

As an illustrative example, ultrasound images can be rendered using PHI as described above and illustrated in the example of FIGS. 12A through 12F.

Figures 12A, 12B, 12C:
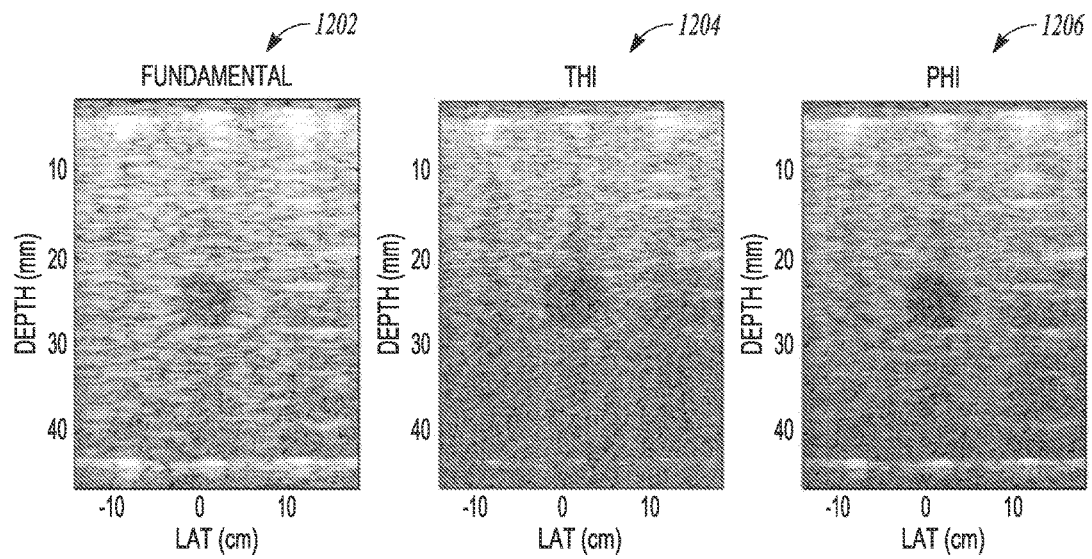
FIG. 12A illustrates generally an illustrative example of an ultrasound image of a phantom obtained using a fundamental frequency technique.
FIG. 12B illustrates generally an illustrative example of an ultrasound image of the phantom obtained using a tissue-harmonic-imaging technique.
FIG. 12C illustrates generally an illustrative example of an ultrasound image of the phantom obtained using a principal-harmonic-imaging technique.

FIG. 12A illustrates generally an illustrative example of an ultrasound image 1202 of a phantom obtained using a fundamental frequency technique, FIG. 12B illustrates generally an illustrative example of an ultrasound image 1204 of the phantom obtained using a tissue-harmonic-imaging technique, and FIG. 12C illustrates generally an illustrative example of an ultrasound image 1206 of the phantom obtained using a principal-harmonic-imaging technique.

Figures 12D, 12E, 12F:
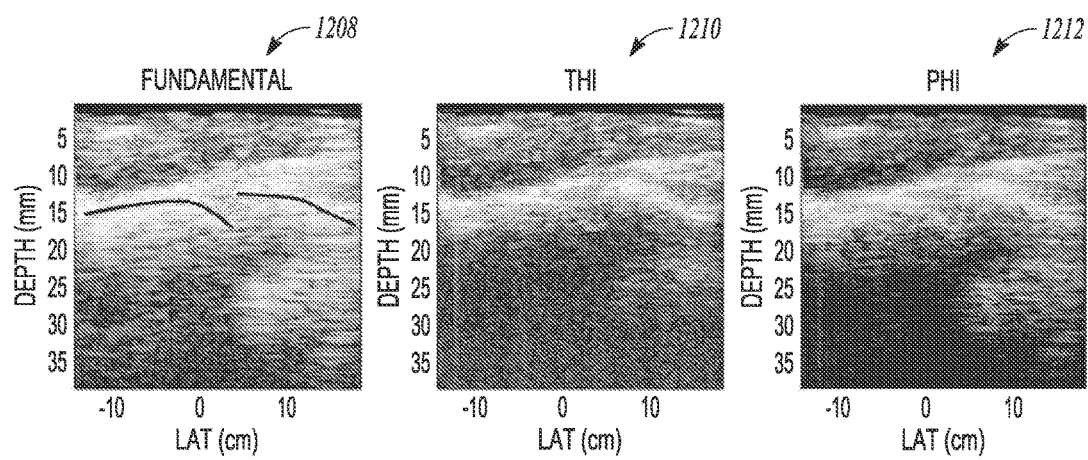
FIG. 12D illustrates generally an illustrative example of an ultrasound image of an in vivo elbow joint obtained using a fundamental frequency technique.
FIG. 12E illustrates generally an illustrative example of an ultrasound image of the in vivo elbow joint obtained using a tissue-harmonic-imaging technique.
FIG. 12F illustrates generally an illustrative example of an ultrasound image of the in vivo elbow joint obtained using a principal-harmonic-imaging technique.

FIG. 12D illustrates generally an illustrative example of an ultrasound image 1208 of an in vivo elbow joint obtained using a fundamental frequency technique, FIG. 12E illustrates generally an illustrative example of an ultrasound image 1210 of the in vivo elbow joint obtained using a tissue-harmonic-imaging technique, and FIG. 12F illustrates generally an illustrative example of an ultrasound image of the in vivo elbow joint obtained using a principal-harmonic-imaging technique 1212.

For example, raw radiofrequency ultrasound echo data can be acquired from an Ultrasonix RP scanner and an L14-5 linear array transducer when imaging an RMI 404GS phantom (as shown in the illustrative examples of FIGS. 12A through 12C) or an in vivo elbow joint (as illustrated in the illustrative examples of FIGS. 12D through 12F). In these illustrative examples, the center frequency was 4 MHz for the Ultrasonix RP scanner. PHI, THI, and fundamental image reconstruction techniques can be compared.

In phantom images of FIGS. 12A through 12C, PHI can provide >3 dB improvement in cystic contrast-to-noise ratio (CNR) over THI with greatly enhanced detection of wire targets located at about 45 mm depth. Similar trends can observed in in vivo images FIGS. 12D through 12F where sharper contrast and reduced clutter and noise can be observed for bone structures where images can be reconstructed with PHI. Compared with imaging at the fundamental frequency, both PHI and THI can yield comparable gains in resolution. However, PHI can additionally reduce reverberation clutter artifact, improve resolution, and can provide sharper delineation of bone surfaces, and piston transducer geometries can be demonstrated to additionally reduce off-axis specular reflection artifact. Thus, in an example, a combination of large, approximately circular transducer geometry and PHI, as illustrated in examples above, can provide improved bone imaging with ultrasound as compared to using an array, using THI, or using fundamental frequency imaging.

In an illustrative example, a multi-modality position sensing approach can be used in combination with one or more of the techniques or apparatus discussed above. For example, an approach can combine estimates from one or more of optical finger navigation (OFN) and ultrasonic position estimates. Such combined estimates can be used to yield a new estimate with lower bias and variance such as via determining a maximum likelihood estimate assuming independently Gaussian-distributed errors. In an illustrative example, custom electronics can for two OFN sensors that can be integrated into apparatus as apparatus shown in FIGS. 2A and 2B.

In an illustrative example, the bias and standard deviation from a multi-modality position sensing technique using OFN and ultrasound measurements can provide bias and standard deviation at 0.037 mm and 0.189 mm respectively, such as for 2 mm translations. In an example, an optical camera can used with or without OFN and ultrasound measurements to yield a position estimate. One or more of illumination or filtering can be provided to preferentially image the target area with specific light wavelengths.

One or more of the apparatus and techniques described in examples above can include a mechanically scanned piston transducer (e.g., a transducer configured with a ⅜" diameter, a 5 MHz center operating frequency, and a 5 cm focal depth, or using one or more other center frequencies or focal depths), such as a transducer obtained from Interson, Pleasanton, Calif., USA.

An Illustrative Example of Motion Estimation that can Include an Echo Decorrelation Technique Speckle tracking and decorrelation-based methods can be used to track motion using ultrasound data, for azimuthal and elevational motion respectively. However, for sector-scan transducers, with azimuthal motion the point spread function (PSF) can rotate, such as causing rapid decorrelation and degraded motion estimation. A sector scan transducer can provide two or more differently-angled scan beams (e.g., to provide ultrasonic energy in at least two directions), such as each having a different angle with respect to a direction of tissue (or other target) motion.

A complex RF decorrelation can vary with the angle between the scan beam and the tissue motion direction. Thus, the present inventors have recognized, among other things, that the set of complex RF decorrelation data from respective scan beams in respective directions can be used to infer the direction and magnitude of tissue (or other target) motion relative to the imaging apparatus, such as along with transducer orientation.

For example, a Bayesian probabilistic estimator can be constructed, such as having the capability to estimate motion in-plane or out-of-plane, such as individually or contemporaneously, such as along with transducer orientation. Other applications include estimation of dynamic rotations, from such complex decorrelation data. Generally, in various approaches, ultrasound echo information can be used to track azimuthal and elevational (e.g., out-of-plane) motion, such as using speckle tracking and speckle decorrelation methods, respectively.

However, tracking of azimuthal motion using a sector-scanned speckle image can be degraded by rotation of the point-spread function with translation. For instance, rotations of just 2-10 degrees can cause rapid decorrelation. Tracking axial motion using RF data can provide higher resolution than for lateral motion, such as due to the higher spatial frequency in the axial dimension, a smaller speckle size for received complex echo RF data in this dimension, and an ability to use time-delay estimators that can closely approach the Cramer-Rao Lower Bound (CRLB).

Tissue motion can be decomposed into orthogonal axial and lateral components relative to each of the sector scan A-lines (e.g., such "sectors" corresponding to respective directions of transmission or receiving of ultrasound energy). Therefore, when in-phase/quadrature (IQ) signals are used, the complex inter-frame correlation data for each A-line can include information from which one or more of the axial and lateral components of motion can be estimated. In an example, a probabilistic, Bayesian maximum likelihood estimator of motion and orientation can use the angular spread of sector-scanned A-lines.

For example, when a transducer is moved relative to tissue containing fully-developed speckle, the correlation between samples from a focused A-line before and after the translation is governed by the correlation of the 3-dimensional PSFs at the start and end locations. Using complex echo RF data, rather than detected signal correlation, can result in increased accuracy in both lateral and axial directions, with a much greater increase in accuracy in the axial direction such as due to the presence of phase data.

Generally, sector-scan ultrasound systems have PSFs that are rotated between different A-lines. For an angled A-line (e.g., making an angle $\phi \neq 0$ with respect to an axial or 2-dimension), this changes the correlation curves for both lateral and axial motion due to geometric projection. For example, projection of a wavevector, "$k=2\pi/\lambda$," onto the axial and lateral axes can introduce a phase factor, "$\exp(j\, 2\pi/\lambda\, \Delta x \sin \phi)$," into the lateral correlation measurement, and can modify the axial phase factor, "$\exp(j\, 2\pi/\lambda\, \Delta x \cos \phi)$," where $\Delta x$ can represent a scalar displacement.

This relationship illustrates that angled A-lines can be used to increase the accuracy of lateral motion estimates. A transducer motion vector with elevational or lateral components will make a different angle, "$\phi_i$," with each of the angled A-lines, providing a diverse set of complex decorrelation curves, as a function of motion, transducer orientation, and A-line geometry. A Bayesian maximum likelihood estimator for the motion vector and transducer orientation can be formed. In this manner, an absolute orientation of the transducer can be detected during motion, rather than just a change in orientation.

Figure 13:
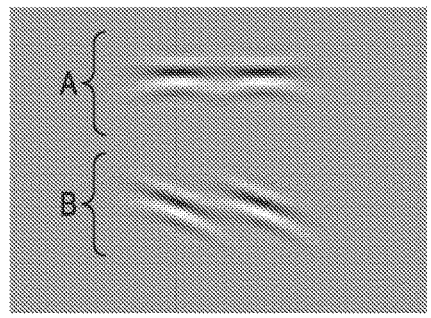
FIG. 13 illustrates generally an illustrative example of angled and non-angled A-lines that can be used for estimation of translation or orientation using an echo decorrelation motion estimation technique.

FIG. 13 illustrates generally an illustrative example of angled A-lines (B) and non-angled A-lines (A) that can be used for estimation of translation or orientation using an echo decorrelation motion estimation technique. For example, a lateral shift complex decorrelation curve can be represented by an autocorrelation of a PSF, such as an approximately Gaussian-shaped representation. For non-angled A-lines (e.g., (B)), a decorrelation can be complex. For example, phase can be linear with shift for small angles, as indicated by the phase factors discussed above. Axial and lateral envelopes can be geometrically projected on a shift direction.

Figure 14A:
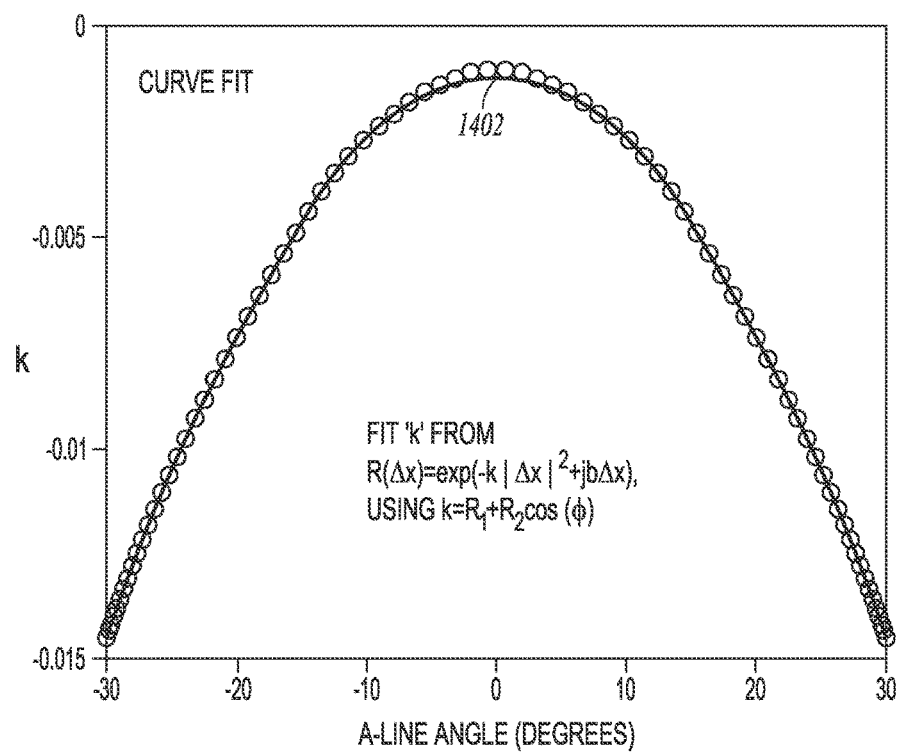
FIG. 14A illustrates generally an illustrative example of a parametric curve fit using simulated A-line information in an echo decorrelation motion estimation technique.
Figure 14B:
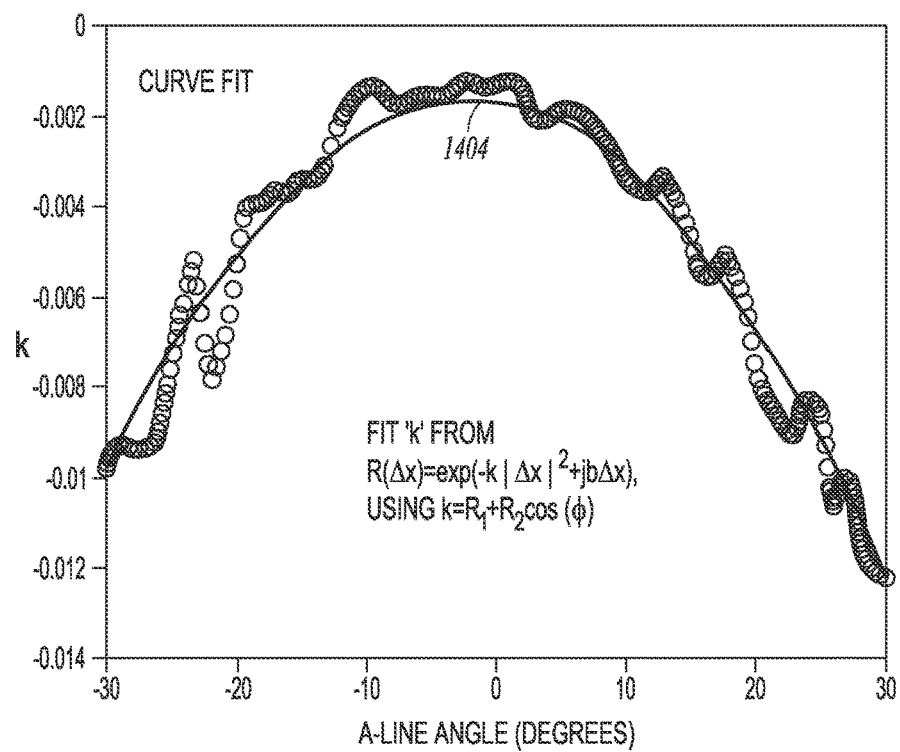
FIG. 14B illustrates generally an illustrative example of a parametric curve fit using experimentally-obtained A-line information in an echo decorrelation motion estimate technique.

FIG. 14A illustrates generally an illustrative example of a parametric curve fit 1402 using simulated A-line information in an echo decorrelation motion estimation technique, and FIG. 14B illustrates generally an illustrative example of a parametric curve fit 1404 using experimentally-obtained A-line information in an echo decorrelation motion estimate technique.

In an illustrative example, a mechanical, 60-degree sector-scanned, piston transducer (Interson, Pleasanton, Calif.) was simulated and used to capture complex (I/Q) experimental data while translated over a tissue mimicking phantom. Simulation in FIELD II were used to characterize variations in complex correlation curves with different motion vectors and transducer orientations.

In this illustrative example, experimental data were used to verify the simulations and empirically sample second-order statistics. Bayes' theorem can be used to relate the conditional probability of a motion vector, "m," such as given a set of observed normalized complex correlations, "r," such as for 50-pixel segments of 256 A-lines at a range of six depths, as in EQN. (3). In this illustrative example, the motion vector m can be defined as a scalar displacement, "$|\Delta s|$," along with 3 angles describing the orientation of the displacement about the axes that can be represented by "$\theta_x$," "$\theta_y$," and "$\theta_z$," as in EQN, (4), with the complex correlation vector also shown with (A-line, depth) indexing. As the evidence probability that can be represented by "P(r)" can be constant for all values of "m," the denominator can be replaced with a proportionality operator in the posterior probability as in EQN. (5). This leads to the maximization over the different candidate m motion vectors, containing the 'prior' probability information P(m), shown in EQN. (6).

$$P(m|r) = P(r|m)P(m)/P(r) \tag{3}$$

$$\vec{m} = [|s|\theta_x, \theta_y, \theta_z]^T, \vec{r} = [r_{1,1} \ldots r_{1,256} r_{2,1} \ldots r_{2,256} r_{6,1} \ldots r_{6,256}]^T \tag{4}$$

$$P(m|r) \alpha P(r|m) P(m) \tag{5}$$

$$\arg\max(m)[P(r|m)P(m)] \tag{6}$$

In an example, if the probability distributions, "P(r|m)," are normally distributed with known first order statistics, the maximization of EQN. (6) can be converted to minimization of a Euclidean distance measure (e.g., a log-likelihood), which can be a computationally simpler approach. Although the probability distributions are not strictly normally distributed, approximation with a normal distribution can be used.

A model can be derived of the complex correlation that can be represented by "$r_{i,j}$," such as for a segment of 50 pixels from the A-line acquired at the 'i'-th angle, at depth "j," for a translation "s" making an angle "$\alpha_1$" with the A-line axial direction vector, shown in EQN. (7). The depth-dependent elements "$a_j(\alpha_i)$" and "$b_j$" can be a function and a depth-related constant respectively, with "$a_j(\alpha_i)$" represented as in EQN. (8), such as including experimentally-determined constants "$R_{1,j}$" and "$R_{2,j}$."

$$r_{i,j} = \exp(a_j(\alpha_i)|s|^2 + jb_j(\pi/2 - \alpha_i)s) \tag{7}$$

$$a(\alpha_i) = R_{1,j} \sin(\alpha) - R_{2,j} \tag{8}$$

Using the model and second-order statistics derived from experimentally-determined data, motion estimation performance was tested using experimental values for r during known translations in the x-y (azimuthal-elevational plane). A log-likelihood maximization corresponding to EQN. (6) was performed for a range of candidate motion vectors m, including x-y motion and rotation about the y (e.g., elevation) axis. Interpolation was used to limit the number of candidate motion vectors.

FIGS. 15A through 15C illustrate generally these experimentally-determined illustrative examples. FIG. 15A illustrates generally an illustrative of an azimuthal shift motion estimation determined using various techniques, FIG. 15B illustrates generally an illustrative example of an elevation shift motion estimation determined using various techniques, and FIG. 15C illustrates generally a rotational shift estimation determined using various techniques.

In FIG. 15A, azimuthal motion was estimated using a model with a fixed (and erroneous by 5 degrees) rotation about the elevational axis. Poor performance in this case (denoted by triangles) indicates that rotational degrees of freedom can significantly increase estimation robustness.

An Illustrative Example that can Include a Shape Modeling Technique

Figure 16:
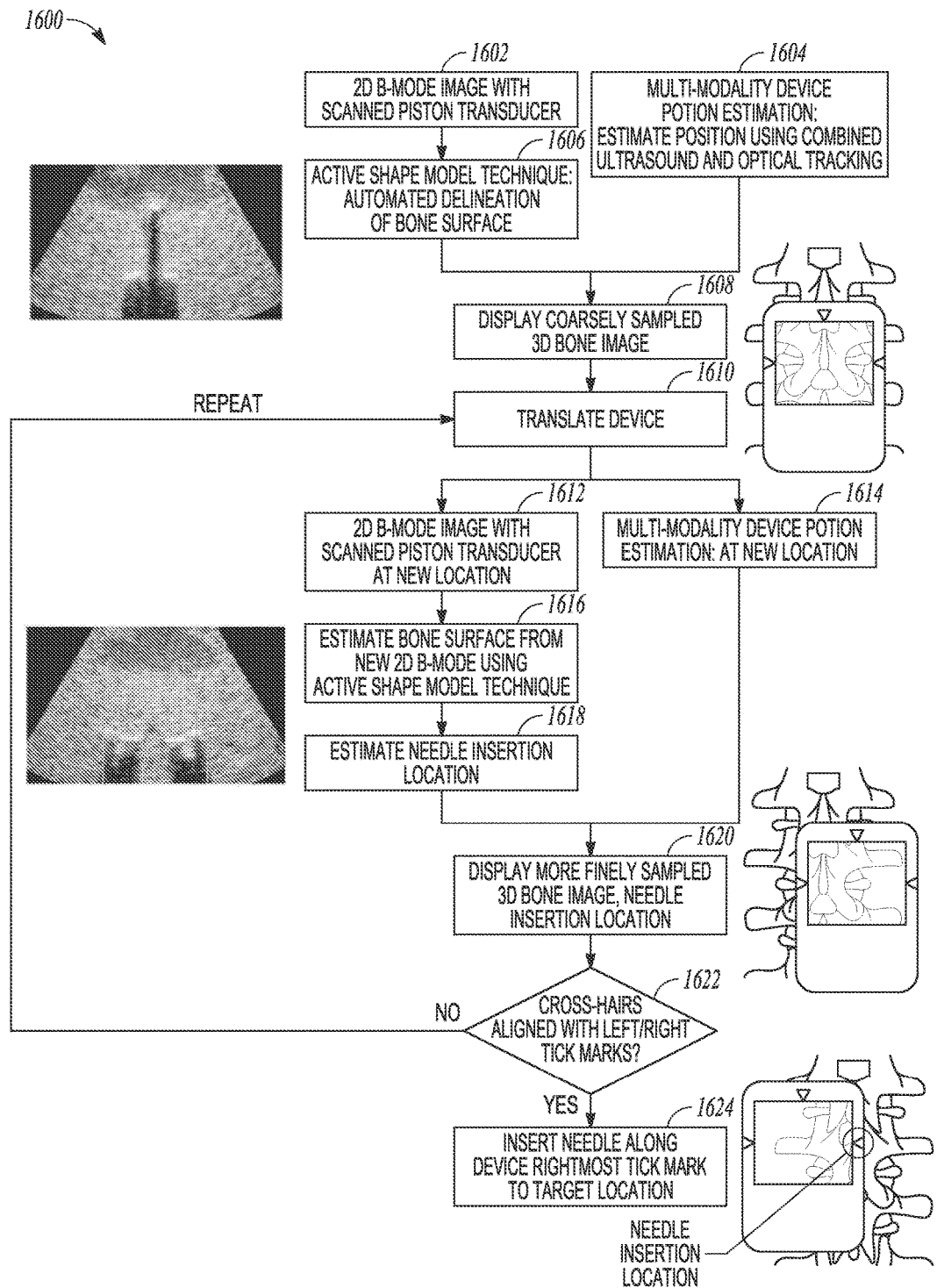
FIG. 16 illustrates generally an illustrative example of a needle-guide technique that can include using a hand-held ultrasound imaging apparatus.

FIG. 16 illustrates generally an illustrative example of a needle-guide technique 1600 that can include using a hand-held ultrasound imaging apparatus, such as including an optical sensor. At 1602, a two-dimensional B-mode image can be obtained such as using a piston transducer. At 1604, a position of the ultrasound imaging apparatus can be estimated using a multi-mode estimate including information obtained from received ultrasound echoes and information obtained via an optical sensor (e.g., a complementary metal-oxide-semiconductor (CMOS) image sensor, a charge-coupled device (CCD), or using one or more other optical sensors). At 1606, an active shape model technique can be used to delineate a bone surface. At 1608, a coarsely-sample three-dimensional bone image can be presented to a user.

At 1610, one or more of an ultrasonic transducer or an apparatus including the transducer can be translated (e.g., a transducer can be mechanical scanned or a fixed transducer can be translated via movement of the assembly, such as movement of a handheld assembly over tissue). At 1612, a new two-dimensional B-mode image can be obtained such as using a piston transducer at the new location. At 1614, a new position of the ultrasound imaging apparatus can be estimated using a multi-mode estimate. At 1616, a bone surface can be estimated using an active shape model technique.

At 1618, a needle insertion location can be estimated. At 1620, a more finely sampled three-dimensional bone image can be presented to the user, including an estimate of the needle insertion location (e.g., a displayed indicium such as a cross-hairs can be presented to the user). At 1622, if the displayed indicium of the needle insertion location is not aligned with one or more fixed indicia located on the housing of the apparatus, the technique 1600 can include returning to 1610 and the apparatus can be translated (e.g., moved slightly) by a user. At 1624, when the displayed indicium is aligned with one or more fixed indicia, a needle can be inserted at a specified location, such as along or nearby a tick mark as shown in the illustrative example of FIG. 16.

In the example of FIG. 16, a statistical signal processing model-fitting strategy can be used, and can be referred to as an "active shape model." Such an active shape model can be used to automatically segment the surface of a spinal bone from a series of obtained 2D images. The segmented bone surface profile along with the multi-modality position estimates can be used together to build up a three-dimensional image of the bone.

Figure 17:
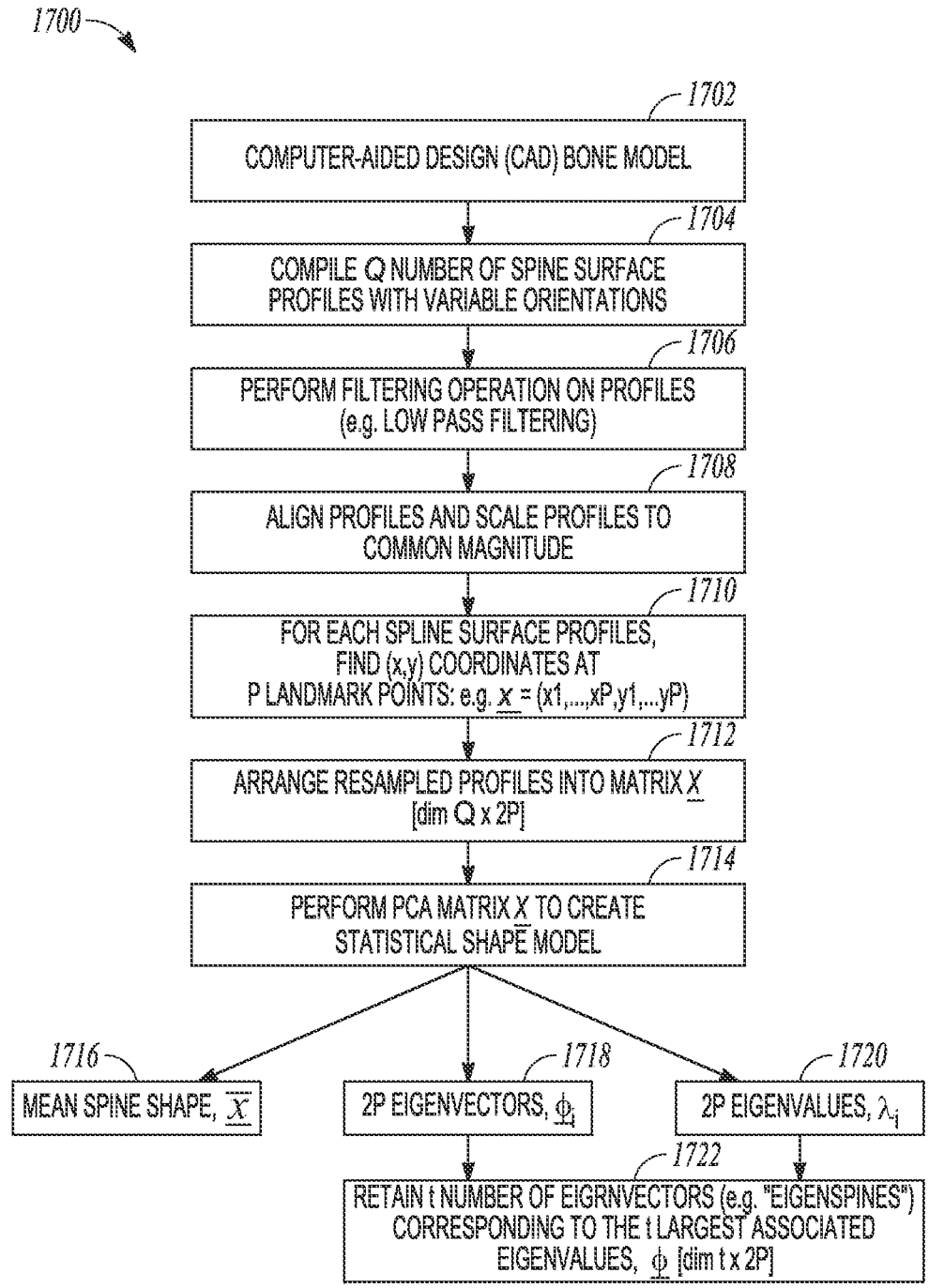
FIG. 17 illustrates generally an illustrative example of a shape-modeling technique.
Figure 18:
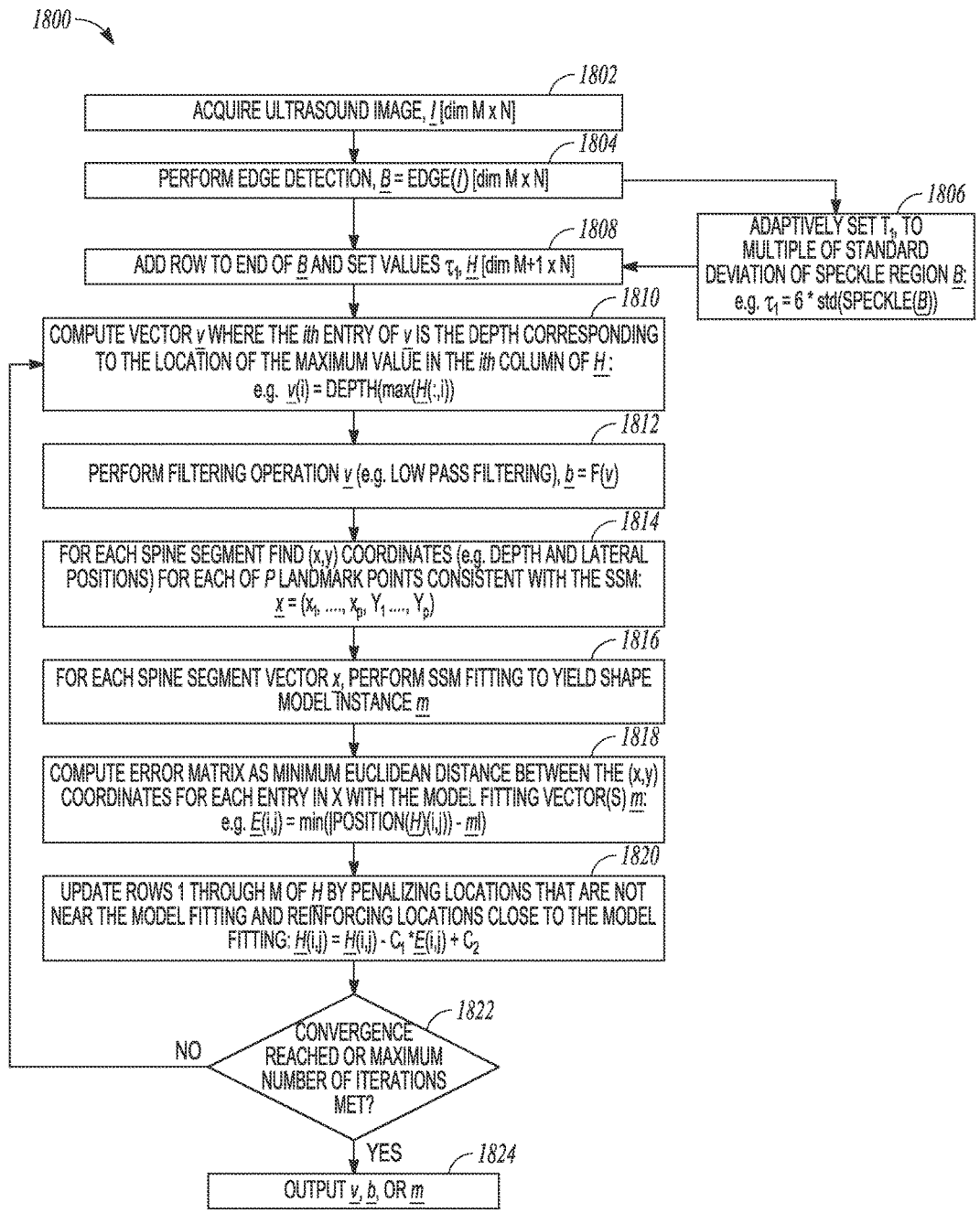
FIG. 18 illustrates generally an illustrative example of a shape-modeling technique.

FIG. 17 illustrates generally an illustrative example 1700 of a shape-modeling technique. The shape model technique 1700 illustrated in FIG. 17 can be used in an active shape modeling technique as shown in FIG. 18, such as to determine a segmentation profile solution, "v," that can maximize a strength of an edge in the image from edge detection, "B," and can minimize an error between the profile solution and a statistical shape model fitting, m:

$$v = \max \lfloor |B(v) - C_1|v - m| + C_2| \rfloor \quad (9)$$

where v can represent the segmentation solution, "B(v)" can represent values of an edge detection image at the segmentation solution location, "m" can represent a solution from a statistical model fitting applied to vector v (or a filtered version of v as in FIG. 18), and $C_1$ and $C_2$ can be constants.

At 1702, a computer aided design (CAD) can be used as a basis for the model, such as to provide a candidate "target," such as at least a portion of a spine. At 1704, a number of spine surface profiles can be compiled, such as corresponding to respective orientations of at least a portion of the spine.

At 1706, a filtering operation can be performed on the respective profiles, such as including low-pass filtering. At 1708, one or more profiles can be aligned or scaled, such as to a common magnitude (e.g., a normalization of the profiles can be performed). At 1710, respective landmark points can be identified, and corresponding (x,y) coordinates for respective landmarks can be determined to provide respective resampled profiles. At 1712, such resampled profiles obtained at 1710 can be arranged into a matrix, that can be represented by "X."

At 1714, a principal components analysis (PCA) can be performed, such as to create a statistical shape model. At 1716, such a shape model can include a "mean" spine shape, at 1718, such a shape model can include respective eigenvectors, and at 1720, such as shape model can include respective eigenvalues. At 1722, a subgroup of eigenvectors can be retained, such as corresponding to the largest associated eigenvalues.

FIG. 18 illustrates generally an illustrative example of a shape-modeling technique 1800. In the illustrative example of FIG. 18, at 1802, ultrasound imaging information can be acquired, and at 1804, an edge detection can be performed on an acquired image. Generally-available shape modeling techniques can have limitations such as that (1), they may not generally be automated; (2) they may assume that the shape of interest is always in the field of view; (3) they may not utilize prior information; (4) training sets may be constructed from a low number of manually segmented images; and (5) they generally may not be used as one of a plurality of factors in an energy function, which can be iteratively maximized or minimized to find a segmented profile.

In contrast, the present inventors have recognized, among other things, that the active shape modeling technique can overcome such limitations. For example, limitation (1) can be addressed, such as in FIG. 18 by fully automating the initialization of the segmentation solution, which can be performed at 1804, 1806, 1808, or 1810. Limitation (2) can be addressed, for example, by using 1808. At 1808, an additional row can added to the image matrix, which can represent the location of "no bone" in the image. If no bone is in the image or if the model fitting vector does not fit well to the proposed segmentation vector, then values in a matrix H can be reduced, and the solution can converge to locations along the artificially created bottom row the matrix. Matrix H can represent the edge detected image B but with a row added to the end, which can be set to a value represented by "$\tau_1$." Thus, the method need not be forced to "find" or segment a bone structure when there is none in the image or if the entire bone is not in the field of view.

At 1812, a filtering operation can be performed on the segmentation profile solution, "v," At 1814, for respective spine segments, (x,y) coordinates (e.g., depth and lateral positions) can be determined for landmark points consistent with a statistical shape model (SSM). At 1816, respective spine segment vectors, "x" can be statistically fitted to yield a statistical shape model fitting, "m." At 1818, an error matrix can be computed, such as using a minimum Euclidean distance between the (x,y) coordinates for respective entries in "x." At 1820, respective rows in H can be updated such as by penalizing locations that are not near the model fitting and reinforcing locations close to the model fitting. At 1822, if convergence has not yet been reached and a maximum number of iterations has not been met, the technique can return to 1810. Otherwise, one or more of "v," "b," or "m," can be output at 1824.

Limitation (4) can be addressed, for example, by using a CAD model as discussed in relation to the example of FIG. 17. Limitation (3) can be addressed, for example, such as by incorporating prior information into the technique illustrated in FIG. 18, such as shown in FIG. 19, which illustrates generally an illustrative example of a shape-modeling technique 1900.

Figure 19:
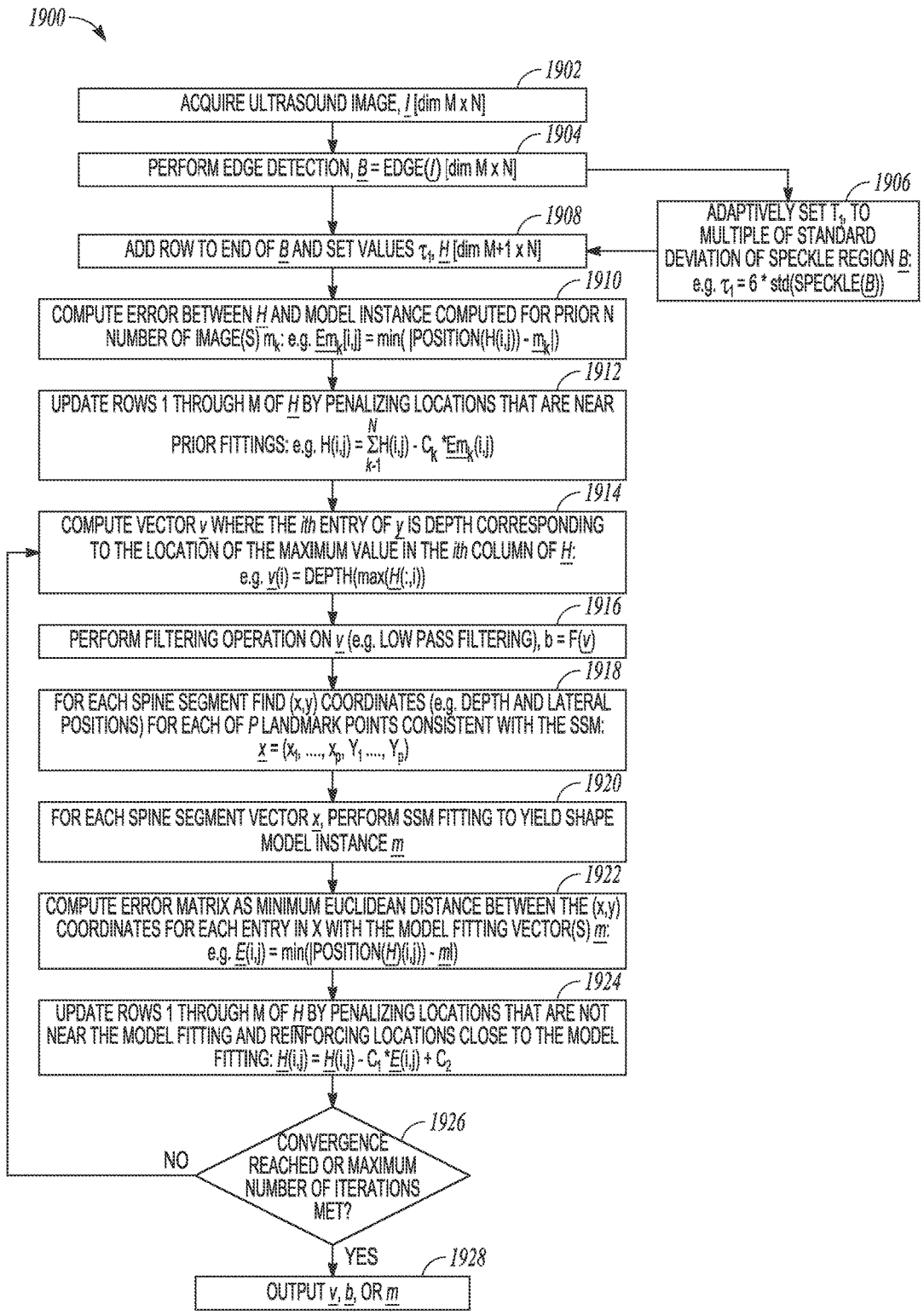
FIG. 19 illustrates generally an illustrative example of a shape-modeling technique.

In the illustrative example of FIG. 19, at 1902, ultrasound imaging information can be acquired, and at 1904, an edge detection can be performed on an acquired image. At 1906, a value can be determined as a multiple of a standard deviation of a speckle region. At 1908, an additional row can added to the image matrix including the value determined at 1906, which can represent the location of "no bone" in the image. At 1910, an error can be computed such as via "pre-weighting" H based on the segmentation results from previous images. The $C_k$ values can be equal for all k at 1912 or they can depend on the distance or time from the current image in which the prior data was acquired. Generally, 1910 and 1912 bias segmentation results toward results achieved from previous images.

As in the illustrative example of FIG. 18, at 1916, a filtering operation can be performed on the segmentation profile solution, "v," At 1918, for respective spine segments, (x,y) coordinates (e.g., a depth and a lateral position) can be determined for landmark points consistent with a statistical shape model (SSM). At 1920, respective spine segment vectors, "x" can be statistically fitted to yield a statistical shape model fitting, "m." At 1922, an error matrix can be computed, such as using a minimum Euclidean distance between the (x,y) coordinates for respective entries in "x." At 1924, respective rows in H can be updated such as by penalizing locations that are not near the model fitting and reinforcing locations close to the model fitting. At 1926, if convergence has not yet been reached and a maximum number of iterations has not been met, the technique can return to 1914. Otherwise, one or more of "v," "b," or "m," can be output at 1928.

Limitation (5) can be addressed such using the techniques of FIG. 18 or 19, such as including iteratively minimizing or maximizing an error function. For example, such techniques can iteratively finds a profile that can minimize error compared with the shape model and maximizes an edge strength such as shown in EQN. (9), such as shown at 1820 or 1924, including an incorporation of an error, "E," such as with an edge strength that can be represented by "H."

Figure 20A:
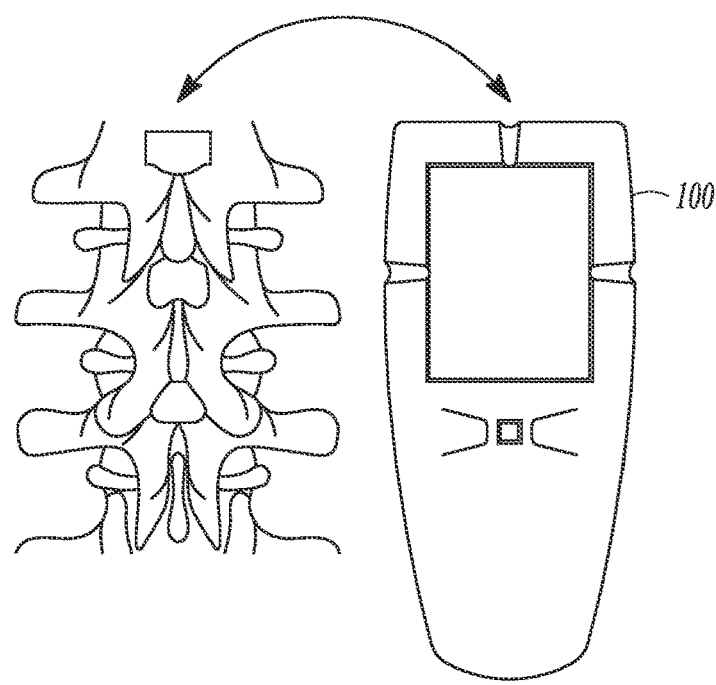
FIGS. 20A through 20G illustrate generally a technique that can include identifying a needle insertion site such as for use in an epidural anesthesia procedure.
Figure 20B:
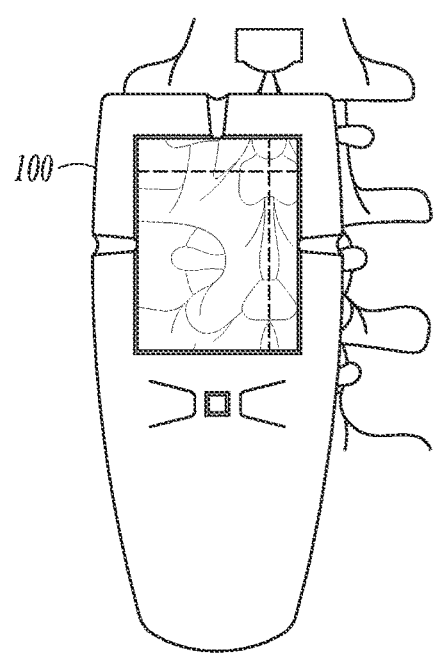
Figure 20C:
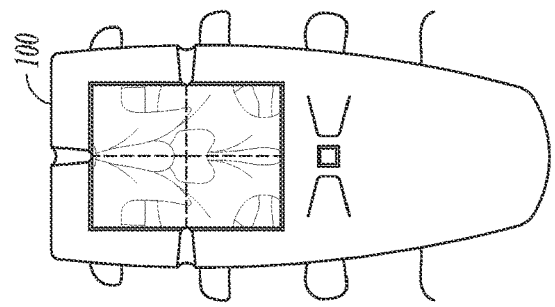
Figure 20D:
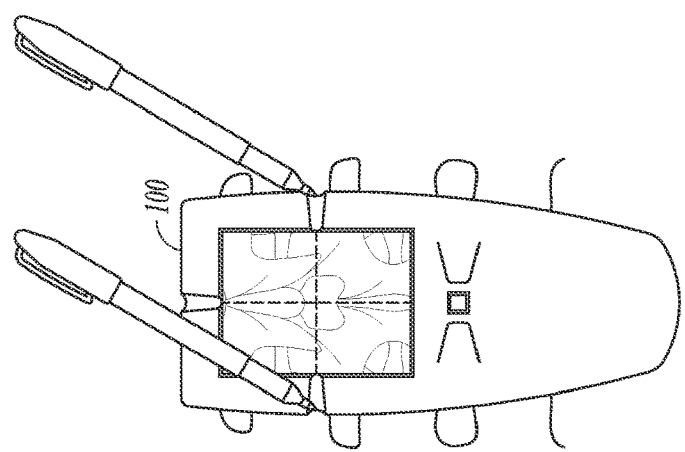
Figure 20E:
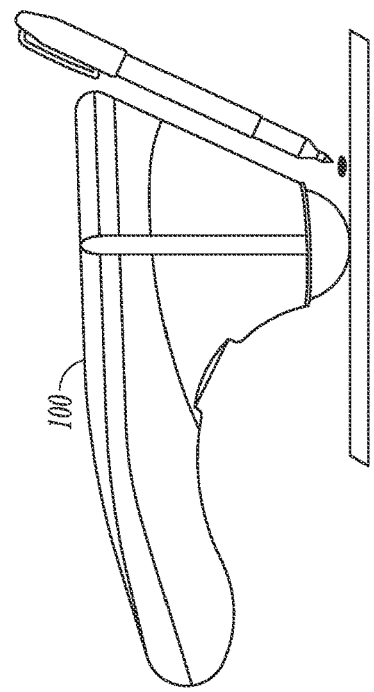
Figure 20F:
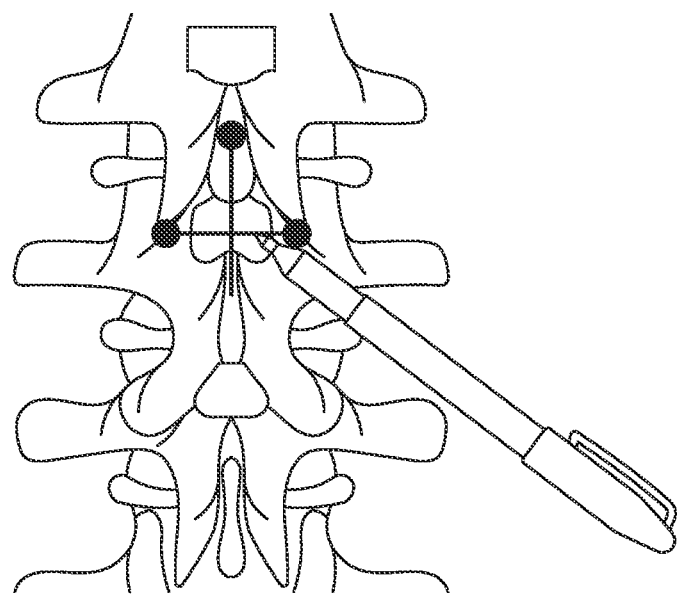
Figure 20G:
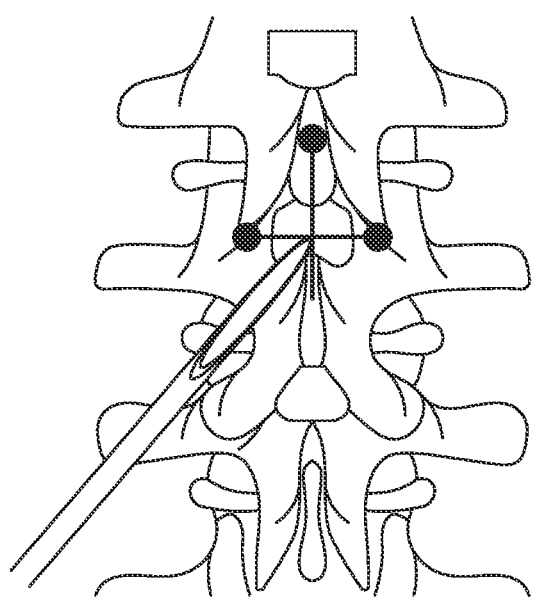

More Illustrative Examples of Needle Insertion Site Identification that can Include an Ultrasound Imaging Technique FIGS. 20A through 20G illustrate generally a technique that can include identifying a needle insertion site such as for use in an epidural anesthesia procedure. In FIG. 20A, an ultrasound imaging apparatus 100 can be coupled to a patient's skin, such as in proximity to a lumbar spine region. In FIG. 20B, the ultrasound imaging apparatus 100 can be translated along a surface of the patient's skin, such as to "build up" a three-dimensional representation of the spine. In FIG. 20C, a cross hairs or other displayed indicia presented to the user on the handheld apparatus 100 can be aligned to one or more of a marking instrument guide or a needle guide located on the housing of the apparatus. In FIG. 20D, a patient's skin can be marked such as using a marking instrument (e.g., a marker or pen) guided by one or more of a needle guide or a marking instrument guide located on the apparatus 100. FIG. 20E illustrates a side view of the apparatus 100 such as shown in FIG. 20D. In FIG. 20F, the apparatus 100 can be removed from the skin, and one or more lines can be extended, such as between two or more marks made using respective marking instrument guides or needle guides, such as shown in FIGS. 20D through 20E. In FIG. 20G, a needle can be inserted, such as at an intersection of two lines respectively extending between marks made at least in part using the apparatus 100 to align a marking instrument. The three-dimensional representation can be constructed using one or more techniques discussed in the examples above or below, and the apparatus can include one or more portions of FIG. 1, or FIGS. 2A through 2B, or one or more other examples.

Figure 21A:
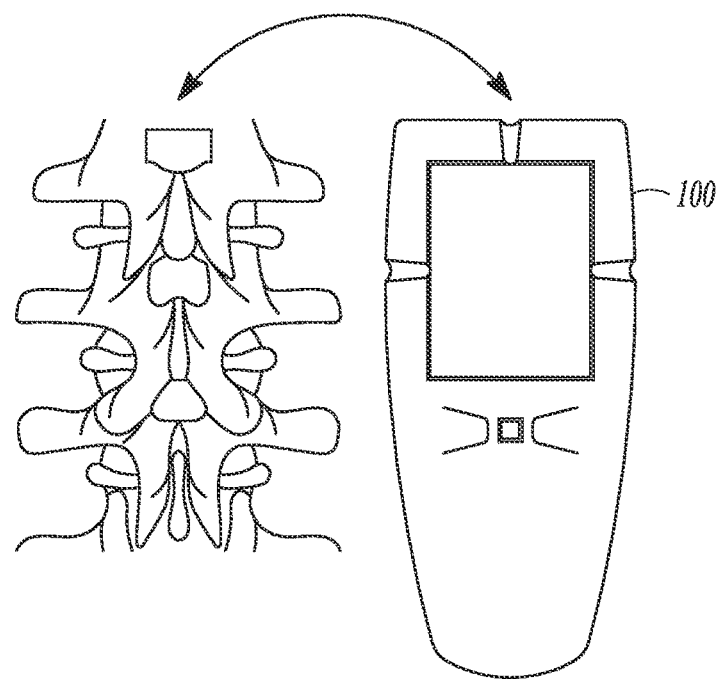
Figure 21B:
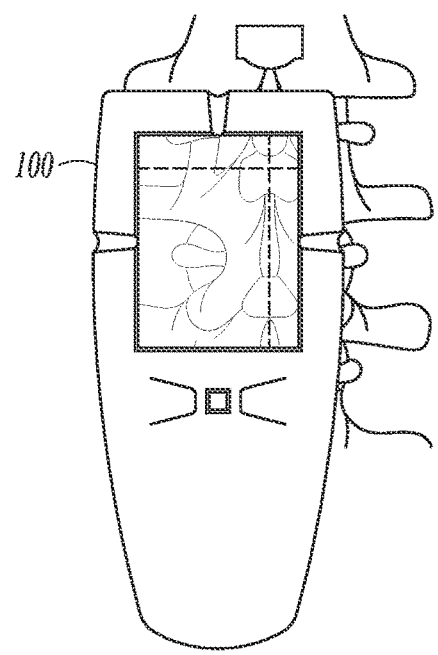

FIGS. 21A through 21E illustrate generally a technique that can include identifying a needle insertion site and performing a needle insertion, such as for use in an epidural anesthesia procedure. In FIG. 21A, an ultrasound imaging apparatus 100 can be coupled to a patient's skin, such as in proximity to a lumbar spine region. In FIG. 21B, the ultrasound imaging apparatus 100 can be translated along a surface of the patient's skin, such as to "build up" a three-dimensional representation of the spine. In FIG. 21C, a cross hairs or other displayed indicia presented to the user on the handheld apparatus 100 can be aligned to one or more of a marking instrument guide or a needle guide located on the housing of the apparatus. In FIG. 21D, a needle can be inserted into the patient's skin, such as while contemporaneously imaging a bone below the skin. Such needle insertion can be aligned using information displayed on the apparatus 100, and using a needle guide included as a portion of the apparatus 100, such as located on the housing. FIG. 21E illustrates a side view of the apparatus 100 such as shown in FIG. 21D. The three-dimensional representation can be constructed using one or more techniques discussed in the examples above or below, and the apparatus can include one or more portions of FIG. 1, or FIGS. 2A through 2B, or one or more other examples.

Various Notes

Example 1 can include or use subject matter (such as an apparatus, a method, a means for performing acts, or a device readable medium including instructions that, when performed by the device, can cause the device to perform acts), such as can include or use an ultrasonic transducer element configured to generate ultrasonic energy to be directed into tissue of a subject and configured to receive a portion of the ultrasonic energy reflected by a predominantly specular-reflecting target, the ultrasonic transducer element comprising a surface configured to provide or receive the ultrasonic energy, the surface including an area of greater than or equal to about $4\lambda^2$, where $\lambda$ is an acoustic wavelength corresponding to a center frequency of the generated ultrasonic energy, the surface at least approximately symmetrical in two axes, a processor circuit configured to control the ultrasonic transducer element to generate or receive ultrasonic energy, and configured to obtain information indicative of the ultrasonic energy reflected by the target, a position tracking circuit configured to provide information indicative of a motion of the ultrasonic transducer element, and a display configured to present information about one or more of a location, orientation, or shape of the target, the information about the location, orientation, or shape determined by the processor circuit using the obtained information indicative of the ultrasonic energy reflected by the target and the information indicative of the motion of the ultrasonic transducer element.

Example 2 can include, or can optionally be combined with the subject matter of Example 1, to optionally include a display substantially parallel to a tissue surface, and the information determined by the processor circuit including providing a spatially-registered three-dimensional representation of at least a portion of the target for presentation via the display.

Example 3 can include, or can optionally be combined with the subject matter of one or any combination of Examples 1 or 2 to optionally include a housing sized and shaped to be held or manipulated using one hand of a user, the housing including the processor circuit, the position tracking circuit, and the display, the ultrasonic transducer located on or within the housing.

Example 4 can include, or can optionally be combined with the subject matter of Example 3, to optionally include a housing including at least one of a needle guide or a guide for a marking instrument, the at least one of the needle guide or the guide for a marking instrument located along or near a perimeter of the display.

Example 5 can include, or can optionally be combined with the subject matter of one or any combination of Examples 3 or 4 to optionally include a housing including at least two fixed alignment indicia at locations specified to align the apparatus with a specified region, the specified region determined at least in part using information about one or more of a location, orientation, or shape of an anatomical feature relative to the display.

Example 6 can include, or can optionally be combined with the subject matter of Example 5, to optionally include at least one of the needle guide or the guide for a marking instrument aligned at least in part using at least one of the alignment indicia.

Example 7 can include, or can optionally be combined with the subject matter of one or any combination of Examples 3 through 6 to optionally include a processor configured to generate an image for presentation via the display including a displayed alignment indicium.

Example 8 can include, or can optionally be combined with the subject matter of Example 7, to optionally include a housing including at least one fixed alignment indicium, and apparatus configured to provide an indication that the apparatus is aligned with a specified region when the displayed alignment indicium is in a specified location relative to the fixed alignment indicium, the specified region determined at least in part using information about a location of an anatomical feature within the tissue relative to a surface of the tissue region.

Example 9 can include, or can optionally be combined with the subject matter of one or any combination of Examples 1 through 8 to optionally include a processor circuit is configured to identify, via the display, an estimate of one or more of a location, orientation, or shape of a specified anatomical feature.

Example 10 can include, or can optionally be combined with the subject matter of one or any combination of Examples 1 through 9 to optionally include a target comprising bone, and a processor circuit configured to estimate one or more of a location, shape, or orientation of the bone using a model including information about a candidate target.

Example 11 can include, or can optionally be combined with the subject matter of one or any combination of Examples 1 through 10 to optionally include one or more of an optical imaging sensor or an accelerometer, and a position tracking circuit configured to determine the information indicative of a motion of the ultrasonic transducer element using information obtained via one or more of the optical imaging sensor or the accelerometer, and information about the received ultrasonic energy.

Example 12 can include, or can optionally be combined with the subject matter of one or any combination of Examples 1 through 11 to optionally include a position tracking circuit configured to estimate one or more of an out-of plane or in-plane motion of the ultrasonic transducer element at least in part using information obtained via the correlation between two or more ultrasonic echo signals received during a specified interval.

Example 13 can include or use subject matter (such as an apparatus, a method, a means for performing acts, or a device readable medium including instructions that, when performed by the device, can cause the device to perform acts), such as can include or use an ultrasonic transducer element array, the army configured to generate ultrasonic energy to be directed into tissue of a subject and configured to receive a portion of the ultrasonic energy reflected by a predominantly specular-reflecting target, and the array including a spacing between at least two adjacent ultrasound transducer elements of less than or equal to about $\frac{1}{2}$ $\lambda$, where $\lambda$ is an acoustic wavelength corresponding to a center frequency of the generated ultrasonic energy, and the array comprising an aperture that is at least approximately symmetrical in two axes, a processor circuit configured to control the ultrasonic transducer array to generate or receive ultrasonic energy, and configured to obtain information indicative of the ultrasonic energy reflected by the target, a display configured to present information about one or more of a location, orientation, or shape of the target, the information about the location, orientation, or shape determined by the processor circuit using the obtained information indicative of the ultrasonic energy reflected by the target.

Example 14 can include, or can optionally be combined with the subject matter of Example 13, to optionally include an array comprising a linear array, an annular array, or a two-dimensional array.

Example 15 can include, or can optionally be combined with the subject matter of one or any combination of Examples 13 or 14 to optionally include a display substantially parallel to a tissue surface, and information determined by the processor circuit including providing a spatially-registered three-dimensional representation of at least a portion of the target for presentation via the display.

Example 16 can include, or can optionally be combined with the subject matter of one or any combination of Examples 13 through 15 to optionally include a housing sized and shaped to be held or manipulated using one hand of a user, the housing including the processor circuit and the display, the array including an ultrasonic transducer located on or within the housing.

Example 17 can include, or can optionally be combined with the subject matter of Example 16, to optionally include a housing including at least one of a needle guide or a guide for a marking instrument, at least one of the needle guide or the guide for a marking instrument located along or near a perimeter of the display.

Example 18 can include, or can optionally be combined with the subject matter of one or any combination of Examples 16 or 17 to optionally include a housing including at least two fixed alignment indicia at locations specified to align the apparatus with a specified region, the specified region determined at least in part using information about one or more of a location, orientation, or shape of an anatomical feature relative to the display.

Example 19 can include, or can optionally be combined with the subject matter of one or any combination of Examples 16 through 18 to optionally include a processor configured to generate an image for presentation via the display including a displayed alignment indicium.

Example 20 can include, or can optionally be combined with the subject matter of one or any combination of Examples 13 through 19 to optionally include a processor circuit configured to identify, via the display, an estimate of a location of a specified anatomical feature.

Example 21 can include, or can optionally be combined with the subject matter of one or any combination of Examples 13 through 19 to optionally include a target comprising bone, the processor configured to estimate a location, shape, or orientation of the bone using a model including information about a candidate target.

Example 22 can include or use subject matter (such as an apparatus, a method, a means for performing acts, or a device readable medium including instructions that, when performed by the device, can cause the device to perform acts), such as can include or use an ultrasonic transducer element configured to generate ultrasonic energy, the ultrasonic energy to be directed into tissue of a subject in a time-varying direction and the ultrasonic transducer element configured to receive a portion of the ultrasonic energy reflected by a target, a processor circuit configured to control the ultrasonic transducer element to generate or receive ultrasonic energy, and configured to obtain information indicative of the ultrasonic energy reflected by the target, a position tracking circuit configured to estimate one or more of the magnitude or direction of a motion between the ultrasonic transducer element and the target using information about a magnitude and a phase of a complex correlation, the complex correlation determined using information about at least two samples of ultrasonic energy reflected by a target and information about a hypothetical complex correlation corresponding to motion of the target relative to at least two directions of generated ultrasonic energy, and a display configured to present information about one or more of a magnitude or direction of the motion between the ultrasonic transducer element and the target.

Example 23 can include, or can optionally be combined with the subject matter of Example 22 to optionally include at least two samples of received ultrasonic energy comprising respective samples corresponding to energy received from respective directions.

Example 24 can include, or can optionally be combined with the subject matter of one or any combination of Examples 22 or 23 to optionally include a predominantly specular-reflecting target.

Example 25 can include, or can optionally be combined with the subject matter of one or any combination of Examples 22 through 24 to optionally include information determined by the processor circuit comprising providing a three-dimensional representation of one or more of a location, orientation, or shape of at least a portion of the target for presentation via the display.

Example 26 can include, or can optionally be combined with the subject matter of one or any combination of Examples 1-25 to include, subject matter (such as an apparatus, a method, a means for performing acts, or a machine readable medium including instructions that, when performed by the machine, that can cause the machine to perform acts), such as can include generating ultrasonic energy to be directed into tissue of a subject and receiving a portion of the ultrasonic energy reflected by a predominantly specular-reflecting target using an ultrasonic transducer element comprising a surface configured to provide or receive the ultrasonic energy, the surface including an area of greater than or equal to about $4\lambda^2$, where $\lambda$ is an acoustic wavelength corresponding to a center frequency of the generated ultrasonic energy, the surface at least approximately symmetrical in two axes, obtaining information indicative of the ultrasonic energy reflected by the target, determining information indicative of a motion of the ultrasonic transducer element, and presenting information about one or more of a location, orientation, or shape of the target, the information about the location, orientation, or shape determined using the obtained information indicative of the ultrasonic energy reflected by the target and the information indicative of the motion of the ultrasonic transducer element.

Example 27 can include, or can optionally be combined with the subject matter of Example 26, to optionally include presenting a spatially-registered three-dimensional representation of at least a portion of the target for presentation via a display oriented substantially parallel to a tissue surface.

Example 28 can include, or can optionally be combined with the subject matter of one or any combination of Examples 1-27 to include, subject matter (such as an apparatus, a method, a means for performing acts, or a machine readable medium including instructions that, when performed by the machine, that can cause the machine to perform acts), such as can include generating ultrasonic energy to be directed into tissue of a subject and receiving a portion of the ultrasonic energy reflected by a predominantly specular-reflecting target using an ultrasonic transducer array including a spacing between at least two adjacent ultrasound transducer elements of less than or equal to about $\frac{1}{2}\lambda$, where $\lambda$ is an acoustic wavelength corresponding to a center frequency of the generated ultrasonic energy, and the array comprising an aperture that is at least approximately symmetrical in two axes, obtaining information indicative of the ultrasonic energy reflected by the target, and presenting information about one or more of a location, orientation, or shape of the target, the information about the location, orientation, or shape determined using the obtained information indicative of the ultrasonic energy reflected by the target.

Example 29 can include, or can optionally be combined with the subject matter of Example 28, to optionally include an array comprising a linear array, an annular array, or a two-dimensional array.

Example 30 can include, or can optionally be combined with the subject matter of one or any combination of Examples 1-29 to include, subject matter (such as an apparatus, a method, a means for performing acts, or a machine readable medium including instructions that, when performed by the machine, that can cause the machine to perform acts), such as can include generating ultrasonic energy to be directed into tissue of a subject in a time-varying direction using an ultrasonic transducer element and receiving a portion of the ultrasonic energy reflected by a target, obtaining information indicative of the ultrasonic energy reflected by the target, estimating one or more of a magnitude or direction of a motion between the ultrasonic transducer element and the target using information about a magnitude and a phase of a complex correlation, the complex correlation determined using information about at least two samples of ultrasonic energy reflected by a target and information about a hypothetical complex correlation corresponding to motion of the target relative to at least two directions of generated ultrasonic energy, and presenting information about one or more of a magnitude or direction of the motion between the ultrasonic transducer element and the target.

Example 31 can include, or can optionally be combined with the subject matter of one or any combination of Examples 1-30 to include, subject matter (such as an apparatus, a method, a means for performing acts, or a machine readable medium including instructions that, when performed by the machine, that can cause the machine to perform acts), such as can include using a model comprising a statistical shape model of a candidate target.

Example 32 can include, or can optionally be combined with the subject matter of one or any combination of Examples 1-31 to include, subject matter (such as an apparatus, a method, a means for performing acts, or a machine readable medium including instructions that, when performed by the machine, that can cause the machine to perform acts), such as can include or can use an ultrasonic transducer element configured to provide energy in a defocused manner.

Example 33 can include, or can optionally be combined with the subject matter of one or any combination of Examples 1-32 to include, subject matter (such as an apparatus, a method, a means for performing acts, or a machine readable medium including instructions that, when performed by the machine, that can cause the machine to perform acts), such as can include or can use a processor circuit configured to estimate a location of a portion of the spine using a loopy belief propagation technique.

Example 34 can include, or can optionally be combined with the subject matter of one or any combination of Examples 1-33 to include, subject matter (such as an apparatus, a method, a means for performing acts, or a machine readable medium including instructions that, when performed by the machine, that can cause the machine to perform acts), such as can include or can use a processor circuit configured to control the ultrasonic transducer element to generate or receive ultrasonic energy, and configured to obtain information indicative of the ultrasonic energy reflected by the target, select a windowed region of information indicative of the ultrasonic energy reflected by the target, the windowed region spanning a half of an acoustic wavelength corresponding to a center frequency of the generated ultrasonic energy, identify two or more principal components (PCs) on the windowed region of information using a spectrum analysis technique, project the information indicative of the ultrasonic energy reflected by the target onto a second principal component included in the identified principal components, the second principal component corresponding to information outside a fundamental band corresponding to the center frequency of the generated acoustic energy, and construct an image of at least a portion of the target using the second principal component.

Example 35 can include, or can optionally be combined with the subject matter of Example 34, to optionally include a spectrum analysis technical comprising a singular spectrum analysis (SSA) technique.

Example 36 can include, or can optionally be combined with any portion or combination of any portions of any one or more of Examples 1-35 to include, subject matter that can include means for performing any one or more of the functions of Examples 1-35, or a machine-readable medium including instructions that, when performed by a machine, cause the machine to perform any one or more of the functions of Examples 1-35.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus, comprising:
an ultrasonic transducer element configured to generate ultrasonic energy to be directed into tissue of a subject and configured to receive a portion of the ultrasonic energy reflected by a target comprising bone, the ultrasonic transducer element comprising a surface configured to provide and receive the ultrasonic energy, the surface including an area of greater than or equal to $4\lambda^2$, where $\lambda$ is an acoustic wavelength corresponding to a center frequency of the generated ultrasonic energy, the surface symmetrical in two axes;
a processor circuit that controls the ultrasonic transducer element to generate and receive ultrasonic energy, and configured to obtain information indicative of the ultrasonic energy reflected by the target, the information including echo data; and
a position tracking circuit that provides information indicative of a motion of the ultrasonic transducer element; and
a display configured to present information about one or more of a location, orientation, or shape of the target, the information about the location, orientation, or shape determined by the processor circuit using the obtained information indicative of the ultrasonic energy reflected by the target and the information indicative of the motion of the ultrasonic transducer element;
an elongated housing including at least one of a needle guide or a guide for a marking instrument, wherein at least one of the needle guide or the guide for a marking instrument is located proximal to a perimeter of the display;
wherein the processor circuit estimates one or more of a location, a shape, or an orientation of the bone by fitting the echo data to a system model describing hypothetical echoes from different bone surfaces corresponding to at least one hypothetical target, the system model generated without requiring ionizing radiation exposure to said subject;
and wherein the processor circuit controls the display to present the estimated location, shape, or orientation of the bone relative to the needle guide or the guide for the marking instrument.

2. The apparatus of claim 1, wherein the display is parallel to a tissue surface; and
wherein the information determined by the processor circuit includes providing a spatially-registered three-dimensional representation of at least a portion of the target for presentation via the display.

3. The apparatus of claim 1 wherein the housing includes the processor circuit, the position tracking circuit, and the display; and
wherein the ultrasonic transducer is located on or within the housing.

4. The apparatus of claim 3, wherein the housing includes at least two fixed alignment indicia at locations specified to align the apparatus with a specified region, the specified region determined at least in part using information about one or more of the location, orientation, or shape of the bone relative to the display.

5. The apparatus of claim 4, wherein at least one of the needle guide or the guide for a marking instrument is aligned at least in part using at least one of the fixed alignment indicia.

6. The apparatus of claim 1, wherein the processor is configured to generate an image for presentation via the display including a displayed alignment indicium.

7. The apparatus of claim 6, wherein the apparatus is configured to provide an indication that the apparatus is aligned with a specified region when the displayed alignment indicium is in a specified location relative to at least one fixed alignment indicium, the specified region determined at least in part using information about the location of the bone within the tissue relative to a surface of the tissue region.

8. The apparatus of claim 1, wherein the processor circuit is configured to identify, via the display, the estimate of one or more of the location, orientation, or shape of the bone.

9. The apparatus of claim 1, comprising one or more of an optical imaging sensor or an accelerometer; and
wherein the position tracking circuit is configured to determine the information indicative of a motion of the ultrasonic transducer element using information obtained via one or more of the optical imaging sensor or the accelerometer, and information about the received ultrasonic energy.

10. The apparatus of claim 1, wherein the position tracking circuit is configured to estimate one or more of an out-of plane or in-plane motion of the ultrasonic transducer element at least in part using information obtained via the correlation between two or more ultrasonic echo signals received during a specified interval.

11. The apparatus of claim 1, wherein the echo data includes a parameterized version of the echo data.

12. The apparatus of claim 11, wherein the system model includes a parametric model that includes at least a portion of a spinal anatomy.

13. The apparatus of claim 1, wherein the processor circuit fits the echo data to the system model by determining a maximum likelihood estimate using a priori information concerning spinal anatomy statistics.

14. The apparatus of claim 1, wherein the system model includes a linear observation model of the at least one hypothetical target.

15. The apparatus of claim 1, wherein the system model includes include a series of hypothetical sub-units of the bone.

16. The apparatus of claim 1, wherein the system model includes an active shape model of the at least one hypothetical target.

17. The apparatus of claim 1, wherein the system model includes a statistical shape model of the at least one hypothetical target.

18. The apparatus of claim 1, wherein the at least one hypothetical target includes a plurality of hypothetical targets.

19. A method, comprising:
generating ultrasonic energy to be directed into tissue of a subject and receiving a portion of the ultrasonic energy reflected by a target comprising bone using an apparatus having an ultrasonic transducer element comprising a surface configured to provide and receive the ultrasonic energy, the surface including an area of greater than or equal to $4\lambda^2$, where $\lambda$ is an acoustic wavelength corresponding to a center frequency of the generated ultrasonic energy, the surface symmetrical in two axes, and wherein the apparatus includes a processor;
with said apparatus, obtaining information indicative of the ultrasonic energy reflected by the target, the information including echo data;
with said apparatus, determining information indicative of a motion of the ultrasonic transducer element;
with said apparatus, presenting an image including a displayed alignment indicium of one or more of a location, orientation, or shape of the target, the displayed alignment indicium of the location, orientation, or shape determined using the obtained information indicative of the ultrasonic energy reflected by the target and the information indicative of the motion of the ultrasonic transducer element;
with said apparatus, providing an indication that the apparatus is aligned with a specified region when the displayed alignment indicium is in a specified location relative to one or more of a marking instrument guide or a needle guide, the marking instrument guide and the needle guide disposed proximal to a perimeter of a display, the display disposed in a housing of the apparatus;
with said apparatus, estimating one or more of a location, a shape, or an orientation of the bone by fitting the echo data to a system model describing hypothetical echoes from different bone surfaces corresponding to at least one hypothetical target, the system model generated without requiring ionizing radiation exposure to said subject; and
with said apparatus, presenting the estimated location, shape, or orientation of the bone relative to the needle guide or the guide for the marking instrument.

20. The method of claim 19, comprising presenting a spatially-registered three-dimensional representation of at least a portion of the target for presentation via a display, the display oriented parallel to a tissue surface when the ultrasonic transducer element contacts the tissue surface, the apparatus including the display.

21. The method of claim 19, wherein the echo data includes a parameterized version of the echo data.

22. The method of claim 21, wherein the system model includes a parametric model that includes at least a portion of a spinal anatomy.

23. The method of claim 19, wherein the processor circuit fits the echo data to the system model by determining a maximum likelihood estimate using a priori information concerning spinal anatomy statistics.

24. The method of claim 19, wherein the system model includes a linear observation model of the at least one hypothetical target.

25. The method of claim 19, wherein the system model includes include a series of hypothetical sub-units of the bone.

26. The method of claim 19, wherein the system model includes an active shape model of the at least one hypothetical target.

27. The method of claim 19, wherein the system model includes a statistical shape model of the at least one hypothetical target.

* * * * *